US010435697B2

(12) United States Patent
Poh et al.

(10) Patent No.: US 10,435,697 B2
(45) Date of Patent: Oct. 8, 2019

(54) RECOMBINANT EXPRESSION SYSTEM THAT SENSES PATHOGENIC MICROORGANISMS

(71) Applicant: Nanyang Technological University, Singapore (SG)

(72) Inventors: Chueh Loo Poh, Singapore (SG); Premkumar Jayaraman, Singapore (SG); Maciej Bartosz Holowko, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 78 days.

(21) Appl. No.: 15/524,172

(22) PCT Filed: Nov. 3, 2015

(86) PCT No.: PCT/SG2015/050428
§ 371 (c)(1),
(2) Date: May 3, 2017

(87) PCT Pub. No.: WO2016/072936
PCT Pub. Date: May 12, 2016

(65) Prior Publication Data

US 2017/0335333 A1 Nov. 23, 2017

(30) Foreign Application Priority Data

Nov. 3, 2014 (SG) ............................ 10201407155S

(51) Int. Cl.

| | |
|---|---|
| ***C12N 15/70*** | (2006.01) |
| ***C12N 15/63*** | (2006.01) |
| ***C12N 15/74*** | (2006.01) |
| ***A01N 63/02*** | (2006.01) |
| ***A61K 35/741*** | (2015.01) |
| *A61K 38/00* | (2006.01) |
| *C12Q 1/04* | (2006.01) |

(52) U.S. Cl.
CPC ............. *C12N 15/70* (2013.01); *A01N 63/02* (2013.01); *A61K 35/741* (2013.01); *C12N 15/63* (2013.01); *C12N 15/74* (2013.01); *A61K 38/00* (2013.01); *C12Q 1/04* (2013.01); *Y02A 50/471* (2018.01)

(58) Field of Classification Search
None
See application file for complete search history.

(56) References Cited

U.S. PATENT DOCUMENTS

| | | | | |
|---|---|---|---|---|
| 5,202,420 A * | 4/1993 | Zasloff | ............... | C07K 14/4723 530/300 |
| 6,849,714 B1 * | 2/2005 | Bridon | ................. | C07K 1/1077 530/320 |
| 2012/0027786 A1 | 2/2012 | Gupta et al. | | |

FOREIGN PATENT DOCUMENTS

| | | | | |
|---|---|---|---|---|
| EP | 2557163 | * | 2/2013 | |
| WO | WO200300842 | * | 1/2003 | |
| WO | WO-2006017929 A1 | * | 2/2006 | ........... C07K 14/245 |
| WO | WO2006177929 | * | 2/2006 | |
| WO | WO2006069601 | * | 7/2006 | |
| WO | WO-2006069610 A2 | * | 7/2006 | ........... C07K 14/245 |
| WO | 2013/191651 A1 | | 12/2013 | |

OTHER PUBLICATIONS

Unterweger et al (PLoS ONE 7 (10), E48320. 2012 ).*
Heidelberg et al (Nature. 2000. 406: 477-482).*
Alanis, "Resistance to Antibiotics: Are We in the Post-Antibiotic Era?," *Arch. Med. Res. 36*:697-705, 2005.
Braat et al., "A Phase I Trial with Transgenic Bacteria Expressing Interleukin-10 in Crohn's Disease," *Clin. Gastroenterol. Hepatol. 4*(6):754-759, 2006.
Brophy et al., "Principles of genetic circuit design," *Nat. Methods 11*(5):508-520, 2014.
"Cholera in Angola—update 5," Jun. 21, 2006, World Health Organization, URL=http://www.who.int/csr/don/2006_06_21/en/, download date May 25, 2017, 3 pages.
Culligan et al., "Probiotics and gastrointestinal disease: successes, problems and future prospects," *Gut Pathogens 1*(19), 2009. (12 pages).
Das et al., "Trend of antibiotic resistance of *Vibrio cholerae* strains from East Delhi," *Indian J. Med. Res. 127*(5):478-482, 2008.

(Continued)

*Primary Examiner* — Jennifer E Graser
(74) *Attorney, Agent, or Firm* — Seed IP Law Group LLP

(57) ABSTRACT

The present invention relates to a recombinant expression system comprising at least: (i) a first nucleotide sequence encoding for at least one protein of a quorum sensing system capable of detecting the presence, amount or both of a microorganism of interest by forming a complex with a marker molecule indicating the presence of said microorganism; (ii) a second nucleotide sequence encoding for at least one antimicrobial peptide, wherein the at least one antimicrobial peptide is effective against the microorganism of interest detected by the at least one protein encoded by the first nucleotide sequence, (iii) a third nucleotide sequence encoding for a genetic inverter that inhibits expression of the second nucleotide sequence, wherein the genetic inverter is under control of an inducible promoter and wherein the inducible promoter is induced if the complex of the at least one protein encoded by the first nucleotide sequence and the marker molecule indicating the presence of said microorganism is below a threshold concentration and is not induced if the complex of the at least one protein encoded by the first nucleotide sequence and the marker molecule indicating the presence of said microorganism exceeds a threshold concentration. Further encompassed is the use of the expression system and cells comprising the expression system of the invention.

12 Claims, 10 Drawing Sheets

Specification includes a Sequence Listing.

(56) References Cited

OTHER PUBLICATIONS

Duan et al., "Engineered bacterial communication prevents *Vibrio cholerae* virulence in an infant mouse model," *PNAS 107*(25):11260-11264, 2010.
Ellis et al., "Diversity-based, model-guided construction of synthetic gene networks with predicted functions," *Nature Biotechnology 27*:465-471, 2009.
Elowitz et al., "A synthetic oscillatory network of transcriptional regulators," *Nature 403*:335-338, 2000.
Feng et al., "Optimizing Genetic Circuits by Global Sensitivity Analysis," *Biophys. J. 87*:2195-2202, 2004.
Focareta et al., "A Recombinant Probiotic for Treatment and Prevention of Cholera," *Gastroenterology 130*(6):1688-1695, 2006.
"The Global Burden of Disease: 2004 Update," World Health Organization, 2004, 160 pages.
"Global epidemics and impact of cholera," World Health Organization, URL=http://www.who.int/topics/cholera/impact/en/, download date May 25, 2017, 2 pages.
Gupta et al., "Genetically Programmable Pathogen Sense and Destroy," *ACS Synth. Biol. 2*:715-723, 2013.
Harrison et al., "Synthetic feedback loop model for increasing microbial biofuel production using a biosensor," *Front. Microbiol. 3*(360):1-9, 2012.
Higgins et al., "The major *Vibrio cholerae* autoinducer and its role in virulence factor production," *Nature 450*(7171):883-886, 2007.
Hoffman et al., "Whole-body imaging of bacterial infection and antibiotic response," *Nat. Protocols 1*:2988-2994, 2007.
Jayawardene et al., "Mode of Action of Vibriocin," *J. Bacteriol. 102*(2):382-388, 1970.
Lo et al., "Designing a synthetic genetic circuit that enables cell density-dependent auto-regulatory lysis for macromolecule release," *Chem. Eng. Sci. 103*:29-35, 2013.
Moghaddam et al., "Comparison of in vitro antibacterial activities of two cationic peptides CM15 and CM11 against five pathogenic bacteria: *Pseudomonas aeruginosa, Staphylococcus aureus, Vibrio cholerae, Acinetobacter baumannii,* and *Escherichia coli," Probiotics & Antimicro. Prot. 4*(2):133-139, 2012.
Ng et al., "Bacterial Quorum-Sensing Network Architectures," *Annu. Rev. Genet. 43*(1):197-222, 2009.
Pasotti et al., "Characterization of a synthetic bacterial self-destruction device for programmed cell death and for recombinant proteins release," *J. Biol. Eng. 5*(8):1-12, 2011.
Reidl et al., *"Vibrio cholerae* and cholera: out of the water and into the host," *FEMS Microbiology Reviews 26*:125-139, 2002.
Sack et al., "Getting Serious about Cholera," *N. Engl. J. Med. 355*(7):649-651, 2006.
Shu et al., "Mammalian Expression of infrared Fluorescent Proteins Engineered from a Bacterial Phytochrome," *Science 324*(5928):804-807, 2009.
Sinclair et al., "Oral vaccines for preventing cholera, "*Cochrane Database Syst. Rev.* 3:CD008603, 2011. (166 pages).
Sorokulova, "Preclinical Testing in the Development of Probiotics: A Regulatory Perspective with *Bacillus* strains as an Example," *Clin. Infect. Dis. 46*(Suppl. 2):S92-95, 2008.
Szallasi et al., *System Modeling in Cellular Biology: From Concepts to Nuts and Bolts,* Boston:MIT Press, 2006. (463 pages).

* cited by examiner

SEQUENCE LISTING

<160> NUMBER OF SEQ ID NOS: 39

<210> SEQ ID NO 1
<211> LENGTH: 144
<212> TYPE: DNA
<213> ORGANISM: Artificial Sequence
<220> FEATURE:
<223> OTHER INFORMATION: pAphA promoter

<400> SEQUENCE: 1
ggtcacaact ttgtggcctt ttgttttaca ttttttcatt attgagaata atgtcagttt 60
ttcgactaat cagcatattt gtattccact ttatgcttat tatttagata tactacgttc 120
cctctgtgat aagtaatgta aagc 144

<210> SEQ ID NO 2
<211> LENGTH: 611
<212> TYPE: DNA
<213> ORGANISM: Vibrio cholerae

<400> SEQUENCE: 2

```
atggacgcat caatcgaaaa acgccctcga actcggctat cgcctcaaaa acgcaaacta     60

caactgatgg aaatcgcgtt ggaagtgttt gctaaacgcg gcattggtcg tggtggtcac    120

gcagatattg ccgagattgc gcaagtctcc gttgcaacag tgttcaacta cttcccaact    180

cgtgaagact tggttgacga tgtgctgaat tttgtggttc gtcagtactc caacttcttg    240

accgatcaca tcgatcttga tttggatgtg aaaaccaacc tacaaactct gtgcaaagag    300

atggtgaaat tggcgatgac cgattgtcac tggctcaaag tctggtttga gtggagtgct    360

tcaacccgtg acgaagtttg gccactgttt gtttccacca accgaactaa ccaactgctg    420

atcagaaaca tgtttatgaa agcgatggag cgtggcgaat tgtgtgagaa acacgatgtc    480

gataacatgg ccagcctgtt ccacggcatc ttctactcca tcttcttaca agtgaaccgt    540

ttaggtgaac aagaagcagt gtataagttg gccgatagct acctcaatat gctgtgtatc    600

tataagaact a                                                         611


<210> SEQ ID NO 3
<211> LENGTH: 102
<212> TYPE: DNA
<213> ORGANISM: Artificial Sequence
<220> FEATURE:
<223> OTHER INFORMATION: CRISPR based genetic  inverter gRNA

<400> SEQUENCE: 3

gacagctagc attgtaccaa gttttagagc tagaaatagc aagttaaaat aaggctagtc     60

cgttatcaac ttgaaaaagt ggcaccgagt cggtgctttt tt                       102


<210> SEQ ID NO 4
<211> LENGTH: 31
<212> TYPE: DNA
<213> ORGANISM: Vibrio cholerae

<400> SEQUENCE: 4

agttggcacg taatctgcat ttattagatt g                                    31


<210> SEQ ID NO 5
<211> LENGTH: 4107
<212> TYPE: DNA
<213> ORGANISM: Artificial Sequence
<220> FEATURE:
<223> OTHER INFORMATION: dead Cas9

<400> SEQUENCE: 5

atggataaga aatactcaat aggcttagct atcggcacaa atagcgtcgg atgggcggtg     60

atcactgatg aatataaggt tccgtctaaa aagttcaagg ttctgggaaa tacagaccgc    120

cacagtatca aaaaaaatct tataggggct cttttatttg acagtggaga gacagcggaa    180

gcgactcgtc tcaaacggac agctcgtaga aggtatacac gtcggaagaa tcgtatttgt    240

tatctacagg agatttttc aaatgagatg gcgaaagtag atgatagttt ctttcatcga     300

cttgaagagt ctttttggt ggaagaagac aagaagcatg aacgtcatcc tattttgga      360

aatatagtag atgaagttgc ttatcatgag aaatatccaa ctatctatca tctgcgaaaa    420

aaattggtag attctactga taaagcggat ttgcgcttaa tctatttggc cttagcgcat    480

atgattaagt ttcgtggtca tttttgatt gagggagatt taaatcctga taatagtgat     540

gtggacaaac tatttatcca gttggtacaa acctacaatc aattatttga agaaaaccct    600

attaacgcaa gtggagtaga tgctaaagcg attctttctg cacgattgag taaatcaaga    660

cgattagaaa atctcattgc tcagctcccc ggtgagaaga aaaatggctt atttgggaat    720
```

-continued

```
ctcattgctt tgtcattggg tttgacccct aattttaaat caaattttga tttggcagaa    780
gatgctaaat tacagctttc aaaagatact tacgatgatg atttagataa tttattggcg    840
caaattggag atcaatatgc tgatttgttt ttggcagcta agaatttatc agatgctatt    900
ttactttcag atatcctaag agtaaatact gaaataacta aggctcccct atcagcttca    960
atgattaaac gctacgatga acatcatcaa gacttgactc ttttaaaagc tttagttcga   1020
caacaacttc cagaaaagta taaagaaatc ttttttgatc aatcaaaaaa cggatatgca   1080
ggttatattg atgggggagc tagccaagaa gaattttata aatttatcaa accaatttta   1140
gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctattttga gaagacaaga agacttttat ccatttttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggtacct accatgattt gctaaaaatt   1800
attaaagata aagatttttt ggataatgaa gaaaatgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttga aatcagatgg ttttgccaat cgcaatttta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatgcc   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta aagtgattac cttaaaatct   2880
aaattagttt ctgacttccg aaaagatttc caattctata aagtacgtga gattaacaat   2940
taccatcatg cccatgatgc gtatctaaat gccgtcgttg gaactgcttt gattaagaaa   3000
tatccaaaac ttgaatcgga gtttgtctat ggtgattata aagtttatga tgttcgtaaa   3060
```

-continued

```
atgattgcta agtctgagca agaaataggc aaagcaaccg caaaatattt cttttactct   3120

aatatcatga acttcttcaa aacagaaatt acacttgcaa atggagagat tcgcaaacgc   3180

cctctaatcg aaactaatgg ggaaactgga gaaattgtct gggataaagg gcgagatttt   3240

gccacagtgc gcaaagtatt gtccatgccc caagtcaata ttgtcaagaa aacagaagta   3300

cagacaggcg gattctccaa ggagtcaatt ttaccaaaaa gaaattcgga caagcttatt   3360

gctcgtaaaa aagactggga tccaaaaaaa tatggtggtt ttgatagtcc aacggtagct   3420

tattcagtcc tagtggttgc taaggtggaa aaagggaaat cgaagaagtt aaaatccgtt   3480

aaagagttac tagggatcac aattatggaa agaagttcct ttgaaaaaaa tccgattgac   3540

tttttagaag ctaaaggata taaggaagtt aaaaaagact taatcattaa actacctaaa   3600

tatagtcttt ttgagttaga aaacggtcgt aaacggatgc tggctagtgc cggagaatta   3660

caaaaaggaa atgagctggc tctgccaagc aaatatgtga atttttata tttagctagt    3720

cattatgaaa agttgaaggg tagtccagaa gataacgaac aaaaacaatt gtttgtggag   3780

cagcataagc attatttaga tgagattatt gagcaaatca gtgaattttc taagcgtgtt   3840

attttagcag atgccaattt agataaagtt cttagtgcat ataacaaaca tagagacaaa   3900

ccaatacgtg aacaagcaga aaatattatt catttattta cgttgacgaa tcttggagct   3960

cccgctgctt ttaaatattt tgatacaaca attgatcgta aacgatatac gtctacaaaa   4020

gaagttttag atgccactct tatccatcaa tccatcactg gtctttatga aacacgcatt   4080

gatttgagtc agctaggagg tgactaa                                       4107
```

```
<210> SEQ ID NO 6
<211> LENGTH: 686
<212> TYPE: PRT
<213> ORGANISM: Vibrio cholerae

<400> SEQUENCE: 6

Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Ala Val Leu Phe Gly Gly Leu Val Phe Arg
    50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
            100                 105                 110

Phe Leu His Ile Leu Leu Val His Asp Thr Arg Val Met Ala Leu Gln
        115                 120                 125

Ala Leu Phe Ser Val Leu Val Ala Tyr Leu Ala Val Tyr Gly Leu Thr
    130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Ile
                165                 170                 175

Ser His Glu Thr Lys Val Ser Ile Ala Lys Thr Phe Gly Ala Gly Ile
            180                 185                 190
```

```
Ala His Glu Met Arg Asn Pro Leu Ser Ala Leu Lys Thr Ser Ile Asp
        195                 200                 205

Val Val Arg Thr Met Ile Pro Lys Pro Gln Thr Ala Ala His Thr Asp
    210                 215                 220

Tyr Ser Leu Asp Ala Gln Glu Leu Asp Leu Leu His Gln Ile Leu Asn
225                 230                 235                 240

Glu Ala Asp Asp Val Ile Tyr Ser Gly Asn Asn Ala Ile Asp Leu Leu
                245                 250                 255

Leu Thr Ser Ile Asp Glu Asn Arg Val Ser Pro Ala Ser Phe Lys Lys
            260                 265                 270

His Ser Val Val Asp Val Ile Glu Lys Ala Val Lys Thr Phe Pro Tyr
        275                 280                 285

Lys Asn Ala Ala Asp Gln His Ser Val Glu Leu Glu Val His Gln Pro
    290                 295                 300

Phe Asp Phe Phe Gly Ser Asp Thr Leu Leu Thr Tyr Ala Leu Phe Asn
305                 310                 315                 320

Leu Leu Lys Asn Ala Phe Tyr Tyr Gln Lys Glu His Phe Ser Val Cys
                325                 330                 335

Ile Ser Ile Glu Gln Thr Ser Glu His Asn Leu Ile Arg Val Arg Asp
            340                 345                 350

Asn Gly Val Gly Ile Ala Pro Glu Met Leu Glu Asp Ile Phe Arg Asp
        355                 360                 365

Phe Tyr Thr Phe Gly Lys Asn Gly Ser Tyr Gly Leu Gly Leu Pro Phe
    370                 375                 380

Cys Arg Lys Val Met Ser Ala Phe Gly Gly Thr Ile Arg Cys Ala Ser
385                 390                 395                 400

Gln Gln Gly Gln Trp Thr Glu Phe Val Leu Ser Phe Pro Arg Tyr Asp
                405                 410                 415

Ser Asp Thr Val Asn Glu Ile Lys Thr Glu Leu Leu Lys Thr Lys Ser
            420                 425                 430

Leu Ile Tyr Ile Gly Ser Asn Gln Ala Ile Val Arg Glu Leu Asn Gln
        435                 440                 445

Leu Ala Val Glu Asp Glu Phe Gly Phe Thr Ala Ile Ser Ala Gln Gln
    450                 455                 460

Ala Val Arg Arg Gln Asp Tyr Glu Phe Glu Phe Asp Leu Ile Leu Leu
465                 470                 475                 480

Asp Leu Asp Asp Ala Thr Ala Gln Gly Glu Leu Leu Pro Lys Leu Glu
                485                 490                 495

Gly Thr Leu Ser Phe Ala Glu Gly Cys Ile Gly Tyr Val Tyr Asp Pro
            500                 505                 510

Gly Lys Thr Tyr Ala Val Asn Ile Asn Arg Tyr Leu Arg Ile Gln Pro
        515                 520                 525

Ile Ser Ile His Ser Ile Leu Arg Lys Pro Arg Lys Ile Ile Glu Arg
    530                 535                 540

Leu Leu Phe Glu Gln Glu Ser Leu Ser Met Asn Arg Asn Val Ile Pro
545                 550                 555                 560

Leu Gln Lys Ser Arg His Glu Arg Arg Ile Leu Val Val Asp Asp Asn
                565                 570                 575

Gln Ser Ile Arg Thr Phe Thr Ala Ile Leu Leu Glu Gln Gln Gly Tyr
            580                 585                 590

Glu Val Val Gln Ala Asn Asp Gly Ser Glu Val Leu Lys His Met Glu
        595                 600                 605
```

```
Ser Gln Asn Ile Asp Leu Val Leu Met Asp Ile Glu Met Pro Asn Val
    610                 615                 620

Gly Gly Leu Glu Ala Thr Arg Leu Ile Arg Asn Ser Glu His Glu Tyr
625                 630                 635                 640

Lys Asn Ile Pro Ile Ile Gly Tyr Thr Gly Asp Asn Ser Pro Lys Thr
                645                 650                 655

Leu Ala Leu Val Gln Thr Ser Gly Met Asn Asp Phe Ile Val Lys Pro
            660                 665                 670

Ala Asp Arg Asp Val Leu Leu Asn Lys Val Ala Ala Trp Val
        675                 680                 685


<210> SEQ ID NO 7
<211> LENGTH: 113
<212> TYPE: PRT
<213> ORGANISM: Vibrio cholerae

<400> SEQUENCE: 7

Met Arg Glu Trp Ile Asn Gln Ser Lys Ile Asp Leu Leu Ala Lys Glu
1               5                   10                  15

Ile Gly Glu Glu Asn Val Pro Ile Leu Val Asn Ile Phe Leu Gly Glu
            20                  25                  30

Leu Asn Asp Tyr Gln Ser Lys Leu Val Ser Asp Thr Val Ala Asp Lys
        35                  40                  45

Leu Gly Tyr Leu Lys Glu Ile Ser His Ala Leu Lys Ser Ser Ala Ala
    50                  55                  60

Ser Phe Gly Ala Asp Arg Leu Cys Ala Lys Ala Val Glu Leu Asp Ser
65                  70                  75                  80

Arg Ala Lys Ser Gly Glu Met Met Asp Ile Ser Leu Glu Val Glu His
                85                  90                  95

Met Leu Glu Leu Leu Lys Gln Thr His Gln Cys Tyr Ser Asp Leu Val
            100                 105                 110

His


<210> SEQ ID NO 8
<211> LENGTH: 455
<212> TYPE: PRT
<213> ORGANISM: Vibrio cholerae

<400> SEQUENCE: 8

Met Val Glu Asp Thr Ala Ser Val Ala Ala Leu Tyr Arg Ser Tyr Leu
1               5                   10                  15

Thr Pro Leu Asp Ile Asp Ile Asn Ile Val Gly Thr Gly Arg Asp Ala
            20                  25                  30

Ile Glu Ser Ile Gly Arg Arg Glu Pro Asp Leu Ile Leu Leu Asp Leu
        35                  40                  45

Arg Leu Pro Asp Met Thr Gly Met Asp Val Leu Tyr Ala Val Lys Glu
    50                  55                  60

Lys Ser Pro Asp Val Pro Ile Val Phe Met Thr Ala His Gly Ser Ile
65                  70                  75                  80

Asp Thr Ala Val Glu Ala Met Arg His Gly Ala Gln Asp Phe Leu Ile
                85                  90                  95

Lys Pro Cys Glu Ala Asp Arg Leu Arg Val Thr Val Asn Asn Ala Ile
            100                 105                 110

Arg Lys Ala Ser Lys Leu Lys Asn Asp Val Asp Asn Lys Asn Gln Asn
        115                 120                 125

Tyr Gln Gly Phe Ile Gly Ser Ser Gln Thr Met Gln Ala Val Tyr Arg
```

```
    130                 135                 140

Thr Ile Asp Ser Ala Ala Ser Ser Lys Ala Ser Ile Phe Ile Thr Gly
145                 150                 155                 160

Glu Ser Gly Thr Gly Lys Glu Val Cys Ala Glu Ala Ile His Ala Ala
                165                 170                 175

Ser Lys Arg Gly Asp Lys Pro Phe Ile Ala Ile Asn Cys Ala Ala Ile
            180                 185                 190

Pro Lys Asp Leu Ile Glu Ser Glu Leu Phe Gly His Val Lys Gly Ala
        195                 200                 205

Phe Thr Gly Ala Ala Thr Glu Arg Gln Gly Ala Ala Glu Ala Ala Asp
    210                 215                 220

Gly Gly Thr Leu Phe Leu Asp Glu Leu Cys Glu Met Asp Leu Asp Leu
225                 230                 235                 240

Gln Thr Lys Leu Leu Arg Phe Ile Gln Thr Gly Thr Phe Gln Lys Val
                245                 250                 255

Gly Ser Ser Lys Met Lys Ser Val Asp Val Arg Phe Val Cys Ala Thr
            260                 265                 270

Asn Arg Asp Pro Trp Lys Glu Val Gln Glu Gly Arg Phe Arg Glu Asp
        275                 280                 285

Leu Tyr Tyr Arg Leu Tyr Val Ile Pro Leu His Leu Pro Pro Leu Arg
    290                 295                 300

Ala Arg Gly Asp Asp Val Ile Glu Ile Ala Tyr Ser Leu Leu Gly Phe
305                 310                 315                 320

Met Ser Lys Glu Glu Gly Lys Asp Phe Val Arg Leu Ser Ala Glu Val
                325                 330                 335

Val Glu Arg Phe Arg Gln Tyr Glu Trp Pro Gly Asn Val Arg Gln Leu
            340                 345                 350

Gln Asn Val Leu Arg Asn Val Val Val Leu Asn Glu Gly Arg Glu Ile
        355                 360                 365

Thr Leu Asp Met Leu Pro Pro Pro Leu Asn Gln Met Ser Ala Pro Ile
    370                 375                 380

Asn Arg Ala Leu Pro Leu Ala His Glu Asn Lys Val Ser Val His Glu
385                 390                 395                 400

Ile Phe Pro Leu Trp Met Thr Glu Lys Gln Ala Ile Glu Gln Ala Ile
                405                 410                 415

Glu Ala Cys Asp Gly Asn Ile Pro Arg Ala Ala Thr Tyr Leu Asp Val
            420                 425                 430

Ser Pro Ser Thr Ile Tyr Arg Lys Leu Gln Thr Trp Asn Glu Lys Val
        435                 440                 445

Lys Glu Lys Glu Lys Glu Arg
    450                 455


<210> SEQ ID NO 9
<211> LENGTH: 120
<212> TYPE: PRT
<213> ORGANISM: Escherichia coli

<400> SEQUENCE: 9

Met Ser Asn Ile Arg Glu Leu Ser Phe Asp Glu Ile Ala Leu Val Ser
1               5                   10                  15

Gly Gly Asn Ala Asn Ser Asn Tyr Glu Gly Gly Gly Ser Arg Ser Arg
            20                  25                  30

Asn Thr Gly Ala Arg Asn Ser Leu Gly Arg Asn Ala Pro Thr His Ile
        35                  40                  45
```

```
Tyr Ser Asp Pro Ser Thr Val Lys Cys Ala Asn Ala Val Phe Ser Gly
    50                  55                  60

Met Val Gly Gly Ala Ile Lys Gly Gly Pro Val Gly Met Thr Arg Gly
65                  70                  75                  80

Thr Ile Gly Gly Ala Val Ile Gly Gln Cys Leu Ser Gly Gly Gly Asn
                85                  90                  95

Gly Asn Gly Gly Gly Asn Arg Ala Gly Ser Ser Asn Cys Ser Gly Ser
            100                 105                 110

Asn Val Gly Gly Thr Cys Ser Arg
        115                 120


<210> SEQ ID NO 10
<211> LENGTH: 20
<212> TYPE: PRT
<213> ORGANISM: Artificial Sequence
<220> FEATURE:
<223> OTHER INFORMATION: synthetic peptide

<400> SEQUENCE: 10

Arg Arg Val Ser Arg Arg Pro Met Arg Arg Tyr Arg Ser Arg Arg Pro
1               5                   10                  15

Arg Arg Leu Val
            20


<210> SEQ ID NO 11
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

Gly Arg Ser Arg Trp Arg Arg Val Ser Arg Arg Phe Met Arg Arg
1               5                   10                  15


<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

Trp Lys Leu Phe Lys Lys Ile Leu Lys Val Leu
1               5                   10


<210> SEQ ID NO 13
<211> LENGTH: 15
<212> TYPE: PRT
<213> ORGANISM: Artificial Sequence
<220> FEATURE:
<223> OTHER INFORMATION: Synthetic peptide

<400> SEQUENCE: 13

Lys Trp Lys Leu Phe Lys Lys Ile Gly Ala Val Leu Lys Val Leu
1               5                   10                  15


<210> SEQ ID NO 14
<211> LENGTH: 23
<212> TYPE: PRT
<213> ORGANISM: Xenopus laevis

<400> SEQUENCE: 14

Gly Ile Gly Lys Phe Leu His Ser Ala Lys Lys Phe Gly Lys Ala Phe
```

```
1               5                   10                  15

Val Gly Glu Ile Met Asn Ser
            20


<210> SEQ ID NO 15
<211> LENGTH: 118
<212> TYPE: PRT
<213> ORGANISM: Escherichia coli

<400> SEQUENCE: 15

Met Lys Lys Arg Gly Ala Phe Leu Gly Leu Leu Leu Val Ser Ala Cys
1               5                   10                  15

Ala Ser Val Phe Ala Ala Asn Asn Glu Thr Ser Lys Ser Val Thr Phe
            20                  25                  30

Pro Lys Cys Glu Asp Leu Asp Ala Ala Gly Ile Ala Ala Ser Val Lys
        35                  40                  45

Arg Asp Tyr Gln Gln Asn Arg Val Ala Arg Trp Ala Asp Asp Gln Lys
    50                  55                  60

Ile Val Gly Gln Ala Asp Pro Val Ala Trp Val Ser Leu Gln Asp Ile
65                  70                  75                  80

Gln Gly Lys Asp Asp Lys Trp Ser Val Pro Leu Thr Val Arg Gly Lys
                85                  90                  95

Ser Ala Asp Ile His Tyr Gln Val Ser Val Asp Cys Lys Ala Gly Met
            100                 105                 110

Ala Glu Tyr Gln Arg Arg
        115


<210> SEQ ID NO 16
<211> LENGTH: 236
<212> TYPE: PRT
<213> ORGANISM: Artificial Sequence
<220> FEATURE:
<223> OTHER INFORMATION: Fusion protein

<400> SEQUENCE: 16

Met Ser Asn Ile Arg Glu Leu Ser Phe Asp Glu Ile Ala Leu Val Ser
1               5                   10                  15

Gly Gly Asn Ala Asn Ser Asn Tyr Glu Gly Gly Gly Ser Arg Ser Arg
            20                  25                  30

Asn Thr Gly Ala Arg Asn Ser Leu Gly Arg Asn Ala Pro Thr His Ile
        35                  40                  45

Tyr Ser Asp Pro Ser Thr Val Lys Cys Ala Asn Ala Val Phe Ser Gly
    50                  55                  60

Met Val Gly Gly Ala Ile Lys Gly Gly Pro Val Gly Met Thr Arg Gly
65                  70                  75                  80

Thr Ile Gly Gly Ala Val Ile Gly Gln Cys Leu Ser Gly Gly Gly Asn
                85                  90                  95

Gly Asn Gly Gly Gly Asn Arg Ala Gly Ser Ser Asn Cys Ser Gly Ser
            100                 105                 110

Asn Val Gly Gly Thr Cys Ser Lys Lys Arg Gly Ala Phe Leu Gly Leu
        115                 120                 125

Leu Leu Val Ser Ala Cys Ala Ser Val Phe Ala Ala Asn Asn Glu Thr
    130                 135                 140

Ser Lys Ser Val Thr Phe Pro Lys Cys Glu Asp Leu Asp Ala Ala Gly
145                 150                 155                 160

Ile Ala Ala Ser Val Lys Arg Asp Tyr Gln Gln Asn Arg Val Ala Arg
                165                 170                 175
```

```
Trp Ala Asp Asp Gln Lys Ile Val Gly Gln Ala Asp Pro Val Ala Trp
            180                 185                 190

Val Ser Leu Gln Asp Ile Gln Gly Lys Asp Asp Lys Trp Ser Val Pro
        195                 200                 205

Leu Thr Val Arg Gly Lys Ser Ala Asp Ile His Tyr Gln Val Ser Val
    210                 215                 220

Asp Cys Lys Ala Gly Met Ala Glu Tyr Gln Arg Arg
225                 230                 235


<210> SEQ ID NO 17
<211> LENGTH: 54
<212> TYPE: DNA
<213> ORGANISM: Artificial Sequence
<220> FEATURE:
<223> OTHER INFORMATION: IPTG inducible promoter

<400> SEQUENCE: 17

aattgtgagc ggataacaat tgacattgtg agcggataac aagatactga gcac           54


<210> SEQ ID NO 18
<211> LENGTH: 68
<212> TYPE: DNA
<213> ORGANISM: Artificial Sequence
<220> FEATURE:
<223> OTHER INFORMATION: ATc inducible promoter

<400> SEQUENCE: 18

cctaattttt gttgacactc tatcgttgat agagttattt taccactccc tatcagtgat     60

agagaaaa                                                              68


<210> SEQ ID NO 19
<211> LENGTH: 238
<212> TYPE: PRT
<213> ORGANISM: Artificial Sequence
<220> FEATURE:
<223> OTHER INFORMATION: GFP

<400> SEQUENCE: 19

Met Arg Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160
```

```
Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235


<210> SEQ ID NO 20
<211> LENGTH: 225
<212> TYPE: PRT
<213> ORGANISM: Artificial Sequence
<220> FEATURE:
<223> OTHER INFORMATION: RFP

<400> SEQUENCE: 20

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
    130                 135                 140

Ala Ser Thr Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Thr Asp Ile Lys Leu Asp Ile Thr Ser His Asn Glu Asp Tyr
        195                 200                 205

Thr Ile Val Glu Gln Tyr Glu Arg Ala Glu Gly Arg His Ser Thr Gly
    210                 215                 220

Ala
225


<210> SEQ ID NO 21
<211> LENGTH: 30
<212> TYPE: DNA
<213> ORGANISM: Artificial Sequence
<220> FEATURE:
<223> OTHER INFORMATION: bacterial promoter

<400> SEQUENCE: 21
```

ctgacgcttt ttatcgcaac tctctactgt 30

<210> SEQ ID NO 22
<211> LENGTH: 57
<212> TYPE: DNA
<213> ORGANISM: Artificial Sequence
<220> FEATURE:
<223> OTHER INFORMATION: promoter

<400> SEQUENCE: 22
gtatatatta aaacattctt gacatcttga aacaaatatg atataatagc aatatat 57

<210> SEQ ID NO 23
<211> LENGTH: 26
<212> TYPE: DNA
<213> ORGANISM: Artificial Sequence
<220> FEATURE:
<223> OTHER INFORMATION: Ribosomal binding site

<400> SEQUENCE: 23
tctagagtca cacaggaaag tactag 26

<210> SEQ ID NO 24
<211> LENGTH: 24
<212> TYPE: DNA
<213> ORGANISM: Artificial Sequence
<220> FEATURE:
<223> OTHER INFORMATION: Ribosomal binding site

<400> SEQUENCE: 24
tctagagtca cacaggacta ctag 24

<210> SEQ ID NO 25
<211> LENGTH: 12
<212> TYPE: DNA
<213> ORGANISM: Artificial Sequence
<220> FEATURE:
<223> OTHER INFORMATION: Ribosomal binding site

<400> SEQUENCE: 25
aaagaggaga aa 12

<210> SEQ ID NO 26
<211> LENGTH: 136
<212> TYPE: DNA
<213> ORGANISM: Artificial Sequence
<220> FEATURE:
<223> OTHER INFORMATION: Ribosomal binding site

<400> SEQUENCE: 26
aggatctcca ggcatcaaat aaaacgaaag gctcagtcga aagactgggc ctttcgtttt 60
atctgttgtt tgtcggtgaa cgctctctac tagagtcaca ctggctcacc ttcgggtggg 120
cctttctgcg tttata 136

<210> SEQ ID NO 27
<211> LENGTH: 879
<212> TYPE: DNA
<213> ORGANISM: Artificial Sequence
<220> FEATURE:
<223> OTHER INFORMATION: L-arabinose-induced promoter

<400> SEQUENCE: 27
ttatgacaac ttgacggcta catcattcac tttttcttca caaccggcac ggaactcgct 60

-continued

```
cgggctggcc ccggtgcatt ttttaaatac ccgcgagaaa tagagttgat cgtcaaaacc    120

aacattgcga ccgacggtgg cgataggcat ccgggtggtg ctcaaaagca gcttcgcctg    180

gctgatacgt tggtcctcgc gccagcttaa gacgctaatc cctaactgct ggcggaaaag    240

atgtgacaga cgcgacggcg acaagcaaac atgctgtgcg acgctggcga tatcaaaatt    300

gctgtctgcc aggtgatcgc tgatgtactg acaagcctcg cgtacccgat tatccatcgg    360

tggatggagc gactcgttaa tcgcttccat gcgccgcagt aacaattgct caagcagatt    420

tatcgccagc agctccgaat agcgcccttc cccttgcccg gcgttaatga tttgcccaaa    480

caggtcgctg aaatgcggct ggtgcgcttc atccgggcga aagaaccccg tattggcaaa    540

tattgacggc cagttaagcc attcatgcca gtaggcgcgc ggacgaaagt aaacccactg    600

gtgataccat tcgcgagcct ccggatgacg accgtagtga tgaatctctc ctggcgggaa    660

cagcaaaata tcacccggtc ggcaaacaaa ttctcgtccc tgatttttca ccacccccctg    720

accgcgaatg gtgagattga gaatataacc tttcattccc agcggtcggt cgataaaaaa    780

atcgagataa ccgttggcct caatcggcgt taaacccgcc accagatggg cattaaacga    840

gtatcccggc agcaggggat cattttgcgc ttcagccat                           879
```

```
<210> SEQ ID NO 28
<211> LENGTH: 28
<212> TYPE: DNA
<213> ORGANISM: Artificial Sequence
<220> FEATURE:
<223> OTHER INFORMATION: Promoter

<400> SEQUENCE: 28

ttgtcaggcc ggaataactc cctataat                                        28


<210> SEQ ID NO 29
<211> LENGTH: 106
<212> TYPE: DNA
<213> ORGANISM: Vibrio cholerae

<400> SEQUENCE: 29

gacccttcta agccgagggt cacctagcca actgacgttg ttagtgaaca ccattgttca     60

cacttataga cggccaatca cacttcttgt ggttggcctt tttttt                   106


<210> SEQ ID NO 30
<211> LENGTH: 7
<212> TYPE: PRT
<213> ORGANISM: Artificial Sequence
<220> FEATURE:
<223> OTHER INFORMATION: Antimicrobial peptide

<400> SEQUENCE: 30

Asn Gly Val Gln Pro Lys Tyr
1               5


<210> SEQ ID NO 31
<211> LENGTH: 10
<212> TYPE: PRT
<213> ORGANISM: Artificial Sequence
<220> FEATURE:
<223> OTHER INFORMATION: Antimicrobial peptide

<400> SEQUENCE: 31

Asn Ala Gly Ser Leu Leu Ser Gly Trp Gly
1               5                   10
```

```
<210> SEQ ID NO 32
<211> LENGTH: 19
<212> TYPE: PRT
<213> ORGANISM: Artificial Sequence
<220> FEATURE:
<223> OTHER INFORMATION: Antimicrobial peptide

<400> SEQUENCE: 32

Leu Ile Ala Gly Leu Ala Ala Asn Phe Leu Pro Lys Leu Phe Cys Lys
1               5                   10                  15

Ile Thr Lys


<210> SEQ ID NO 33
<211> LENGTH: 31
<212> TYPE: PRT
<213> ORGANISM: Artificial Sequence
<220> FEATURE:
<223> OTHER INFORMATION: Antimicrobial peptide

<400> SEQUENCE: 33

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30


<210> SEQ ID NO 34
<211> LENGTH: 291
<212> TYPE: DNA
<213> ORGANISM: Artificial Sequence
<220> FEATURE:
<223> OTHER INFORMATION: Secretory peptide

<400> SEQUENCE: 34

atgagtattg atcgcacttc gcctctgaag cctgtaagca ccgttcaacc gcgcgaaacc     60

actgacgcgc cggtaacgaa cagccgggcg gcaaaaacaa ccgcctccac cagcaccagt    120

gtgacgttaa gcgacgcgca agcaaaactg atgcaacccg gcagcagtga tatcaatctt    180

gaacgtgtcg aagcgttaaa actggcgatt cgtaacggtg aactaaaaat ggacaccggc    240

aaaattgccg atgcgctgat caacgaagcg cagcaagact tgcagagtaa c             291


<210> SEQ ID NO 35
<211> LENGTH: 144
<212> TYPE: DNA
<213> ORGANISM: Artificial Sequence
<220> FEATURE:
<223> OTHER INFORMATION: Secretory peptide

<400> SEQUENCE: 35

atgaaaaaaa taacagggat tattttattg cttcttgcag ccattattct tgctgcatgt     60

caggcaaact atatccgtga tgttcagggc gggacagtat caccgtcgtc aactgctgaa    120

ctgaccggag tggaaacgca gtaa                                           144


<210> SEQ ID NO 36
<211> LENGTH: 534
<212> TYPE: DNA
<213> ORGANISM: Artificial Sequence
<220> FEATURE:
<223> OTHER INFORMATION: gentamicin and kanamycin resistance

<400> SEQUENCE: 36

atgttacgca gcagcaacga tgttacgcag cagggcagtc gccctaaaac aaagttaggt     60

ggctcaagta tgggcatcat tcgcacatgt aggctcggcc ctgaccaagt caaatccatg    120
```

```
agggctgctc ttgatctttt cggtcgtgag ttcggagacg tagccaccta ctcccaacat    180

cagccggact ccgattacct cgggaacttg ctccgtagta agacattcat cgcgcttgct    240

gccttcgacc aagaagcggt tgttggcgct ctcgcggctt acgttctgcc aaagtttgag    300

caggcgcgta gtgagatcta tatctatgat ctcgcagtct ccggcgagca ccggaggcaa    360

ggcattgcca ccgcgctcat caatctcctc aagcatgagg ccaacgcgct tggtgcttat    420

gtgatctacg tgcaagcaga ttacggtgac gatcccgcag tggctctcta tacaaagttg    480

ggcatacggg aagaagtgat gcactttgat atcgacccaa gtaccgccac ctaa          534
```

<210> SEQ ID NO 37
<211> LENGTH: 39
<212> TYPE: DNA
<213> ORGANISM: Artificial Sequence
<220> FEATURE:
<223> OTHER INFORMATION: Antimicrobial peptide

<400> SEQUENCE: 37

```
tggaaactgt ttaaaaaaat tctgaaagtg ctgaaccat                            39
```

<210> SEQ ID NO 38
<211> LENGTH: 203
<212> TYPE: PRT
<213> ORGANISM: Vibrio cholerae

<400> SEQUENCE: 38

```
Met Asp Ala Ser Ile Glu Lys Arg Pro Arg Thr Arg Leu Ser Pro Gln
1               5                   10                  15

Lys Arg Lys Leu Gln Leu Met Glu Ile Ala Leu Glu Val Phe Ala Lys
            20                  25                  30

Arg Gly Ile Gly Arg Gly Gly His Ala Asp Ile Ala Glu Ile Ala Gln
        35                  40                  45

Val Ser Val Ala Thr Val Phe Asn Tyr Phe Pro Thr Arg Glu Asp Leu
    50                  55                  60

Val Asp Asp Val Leu Asn Phe Val Val Arg Gln Tyr Ser Asn Phe Leu
65                  70                  75                  80

Thr Asp His Ile Asp Leu Asp Leu Asp Val Lys Thr Asn Leu Gln Thr
                85                  90                  95

Leu Cys Lys Glu Met Val Lys Leu Ala Met Thr Asp Cys His Trp Leu
            100                 105                 110

Lys Val Trp Phe Glu Trp Ser Ala Ser Thr Arg Asp Glu Val Trp Pro
        115                 120                 125

Leu Phe Val Ser Thr Asn Arg Thr Asn Gln Leu Leu Ile Arg Asn Met
    130                 135                 140

Phe Met Lys Ala Met Glu Arg Gly Glu Leu Cys Glu Lys His Asp Val
145                 150                 155                 160

Asp Asn Met Ala Ser Leu Phe His Gly Ile Phe Tyr Ser Ile Phe Leu
                165                 170                 175

Gln Val Asn Arg Leu Gly Glu Gln Glu Ala Val Tyr Lys Leu Ala Asp
            180                 185                 190

Ser Tyr Leu Asn Met Leu Cys Ile Tyr Lys Asn
        195                 200
```

<210> SEQ ID NO 39
<211> LENGTH: 1368
<212> TYPE: PRT
<213> ORGANISM: Artificial Sequence

```
<220> FEATURE:
<223> OTHER INFORMATION: dCas9

<400> SEQUENCE: 39

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400
```

```
Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815
```

```
Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
```

-continued

```
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365
```

RECOMBINANT EXPRESSION SYSTEM THAT SENSES PATHOGENIC MICROORGANISMS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_520USPC_SEQUENCE_LISTING.txt. The text file is 47 KB, was created on May 3, 2017, and is being submitted electronically via EFS-Web.

FIELD OF THE INVENTION

The invention lies in the field of recombinant expression systems designed for autonomous regulation of the expression of at least one peptide, for instance an antimicrobial peptide and use of such systems, e.g. for detection and/or treatment of infections such as gastrointestinal infections.

BACKGROUND OF THE INVENTION

Gastrointestinal infections are a serious cause of significant morbidity and mortality over the world each year (Culligan et al. 2009). Gastrointestinal infectious diseases are becoming increasing challenging to treat mainly because of the increasing emergence of very dangerous antibiotic resistant microorganisms, also known as 'super bugs'. Further, no new antibiotic classes have been discovered in recent past and pharmaceutical companies have significantly reduced their investment in antimicrobial research (Alanis, 2005). Consequently, there is a critical need to explore and develop new and innovative therapeutics for instance against *Vibrio cholerae*.

Cholera is a very serious and highly infectious disease caused by *V. cholerae*, which infects the human GI tract through transmission by contaminated water and/or food. Cholera-infected patients suffer acute diarrhoea. If they are left untreated, they may die within a few hours. Today, cholera is still prevalent in many developing countries, with the highest rates in Asia (Sack et al, 2006).

Conventional methods of treating cholera include oral rehydration therapy, antibiotic therapy and vaccines. Oral rehydration and antibiotics have been effective in treating cholera, but antibiotic resistant strains are becoming more common (Sack et al. 2006; Shukla et al. 2008). Therefore, antibiotics should not be used as a preventative measure, because this will encourage the spread of resistant strains. Moreover, while oral rehydration therapy is an effective treatment method, it cannot prevent infection. In addition, although two cholera vaccines are available, the vaccines only provide around 50-60% immunity in the first two years (Sinclair et al. 2011). Preventing people from being infected in a cholera epidemic is important, as it will reduce the likelihood of healthy people being infected and further contaminating the environment and other people.

Thus, there remains a need in the art for novel, unconventional antimicrobial strategies —for instance against *V. cholerae*—that can complement current antibiotic therapy, but could also be used as a preventative measure.

SUMMARY OF THE INVENTION

The inventors of the present invention have surprisingly found that the above-formulated need can be met by a recombinant expression system comprising at least:

(i) a first nucleotide sequence encoding for at least one protein of a quorum sensing system capable of detecting the presence, amount or both of a microorganism of interest by forming a complex with a marker molecule indicating the presence of said microorganism;

(ii) a second nucleotide sequence encoding for at least one antimicrobial peptide, wherein the at least one antimicrobial peptide is effective against the microorganism of interest detected by the at least one protein encoded by the first nucleotide sequence, (iii) a third nucleotide sequence encoding for a genetic inverter that inhibits expression of the second nucleotide sequence, wherein the genetic inverter is under control of an inducible promoter and wherein the inducible promoter is induced if the complex of the at least one protein encoded by the first nucleotide sequence and the marker molecule indicating the presence of said microorganism is below a threshold concentration and is not induced if the complex of the at least one protein encoded by the first nucleotide sequence and the marker molecule indicating the presence of said microorganism exceeds a threshold concentration.

A second aspect of the invention includes a recombinant cell comprising a recombinant expression system according to the invention.

A third aspect of the invention includes a method of sensing and killing pathogenic microorganisms, the method comprising contacting the recombinant cell of the invention with the pathogenic microorganism.

In a fourth aspect, the invention is directed at the use of a recombinant expression system comprising at least:

(i) a first nucleotide sequence encoding for at least one protein of a quorum sensing system capable of detecting the presence, amount or both of a microorganism of interest by forming a complex with a marker molecule indicating the presence of said microorganism;

(ii) a second nucleotide sequence encoding for at least one detectable marker, (iii) a third nucleotide sequence encoding for a genetic inverter that inhibits expression of the second nucleotide sequence, wherein the genetic inverter is under control of an inducible promoter and wherein the inducible promoter is induced if the complex of the at least one protein encoded by the first nucleotide sequence and the marker molecule indicating the presence of said microorganism is below a threshold concentration and is not induced if the complex of the at least one protein encoded by the first nucleotide sequence and the marker molecule indicating the presence of said microorganism exceeds a threshold concentration, for detection of at least one type of microorganism.

Further embodiments will be apparent to a person skilled in the art with reference to the following description of various non-limiting embodiments.

BRIEF DESCRIPTION OF THE DRAWINGS

The drawings are not necessarily drawn to scale, emphasis instead generally being placed upon illustrating the principles of various embodiments. In the following description, various embodiments of the invention are described with reference to the following drawings.

Overview of a recombinant expression system—exemplified with *V. cholerae*—and the state of the individual components, if the marker molecule produced by the microorganism is below a threshold concentration.

In the exemplary case of *V. cholerae*, an *E. coli* Nissle strain was engineered to express an antimicrobial peptide and the CqsS/CAI-1 quorum-sensing phosphorelay system of *V. cholerae*. In this system (S)-3-hydroxytridecan-4-one (CAI-1) is the marker molecule and CqsS—the CAI-1 receptor—is part of the first nucleotide sequence. At low cell density of *V. cholerae*, when the concentration of the marker molecule CAI-1 is below the detection limit, i.e. the threshold, CqsS functions as a kinase. Following auto-phosphorylation at His194, the phosphoryl group is transferred to Asp618 on the CqsS receiver domain. The next transfer is to His58 on LuxU. LuxU, in turn, transfers the phosphoryl group to Asp47 on LuxO. Once phosphorylated, LuxO binds to σ54 factor. This complex binds to Qrr4 promoter (pQrr4), which is the inducible promoter controlling the genetic inverter. The genetic inverter in turn negatively regulates expression of the antimicrobial peptide.

Thus, at low cell density of *V. cholerae* production of the antimicrobial peptide is repressed and rapidly started upon CAI-1 detection.

Figure 1:
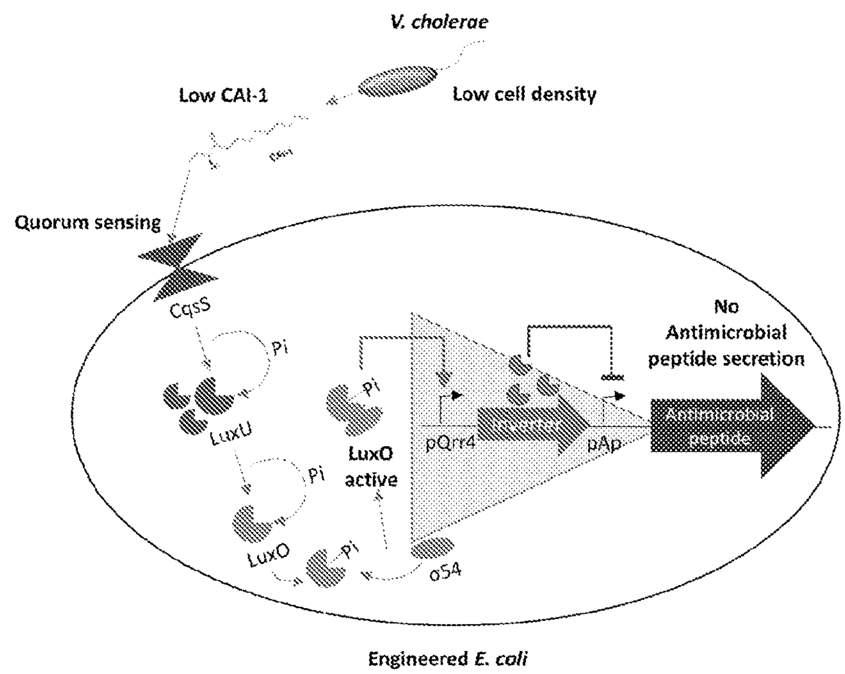
FIG. 1A.
Figure 1B:
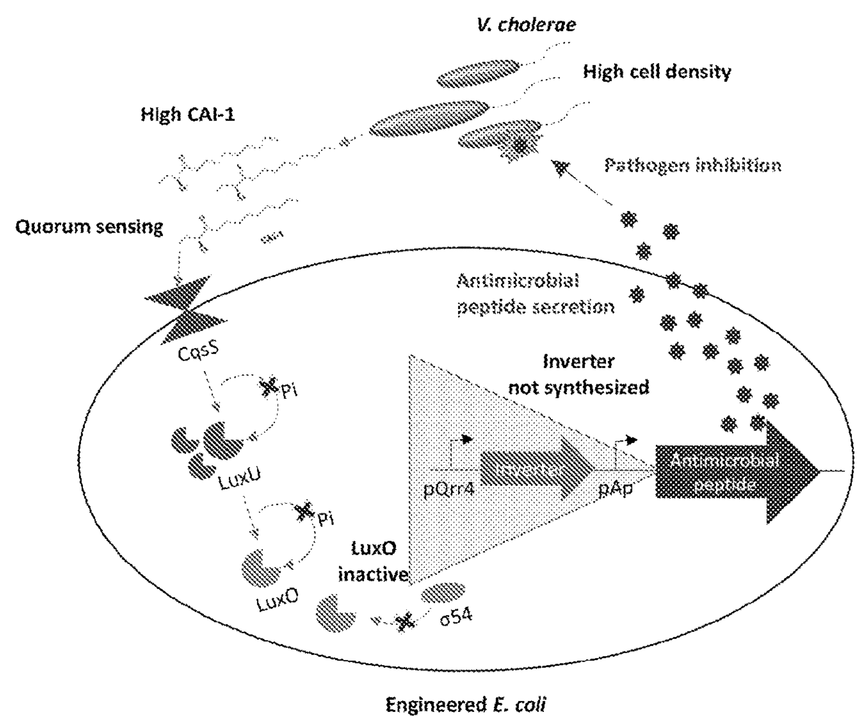

FIG. 1B Overview of a recombinant expression system—exemplified with *V. cholerae*—and the state of the individual components, if the marker molecule produced by the microorganism of interest is exceeding a threshold concentration. At high cell density of *V. cholerae*, the marker molecule CAI-1 accumulates and binds CqsS, and switches CqsS to a phosphatase. Phospho-flow is reversed and LuxO is dephosphorylated. The genetic inverter is not produced, resulting in the synthesis of the antimicrobial peptide, which kills *V. cholerae*.

Figure 2:
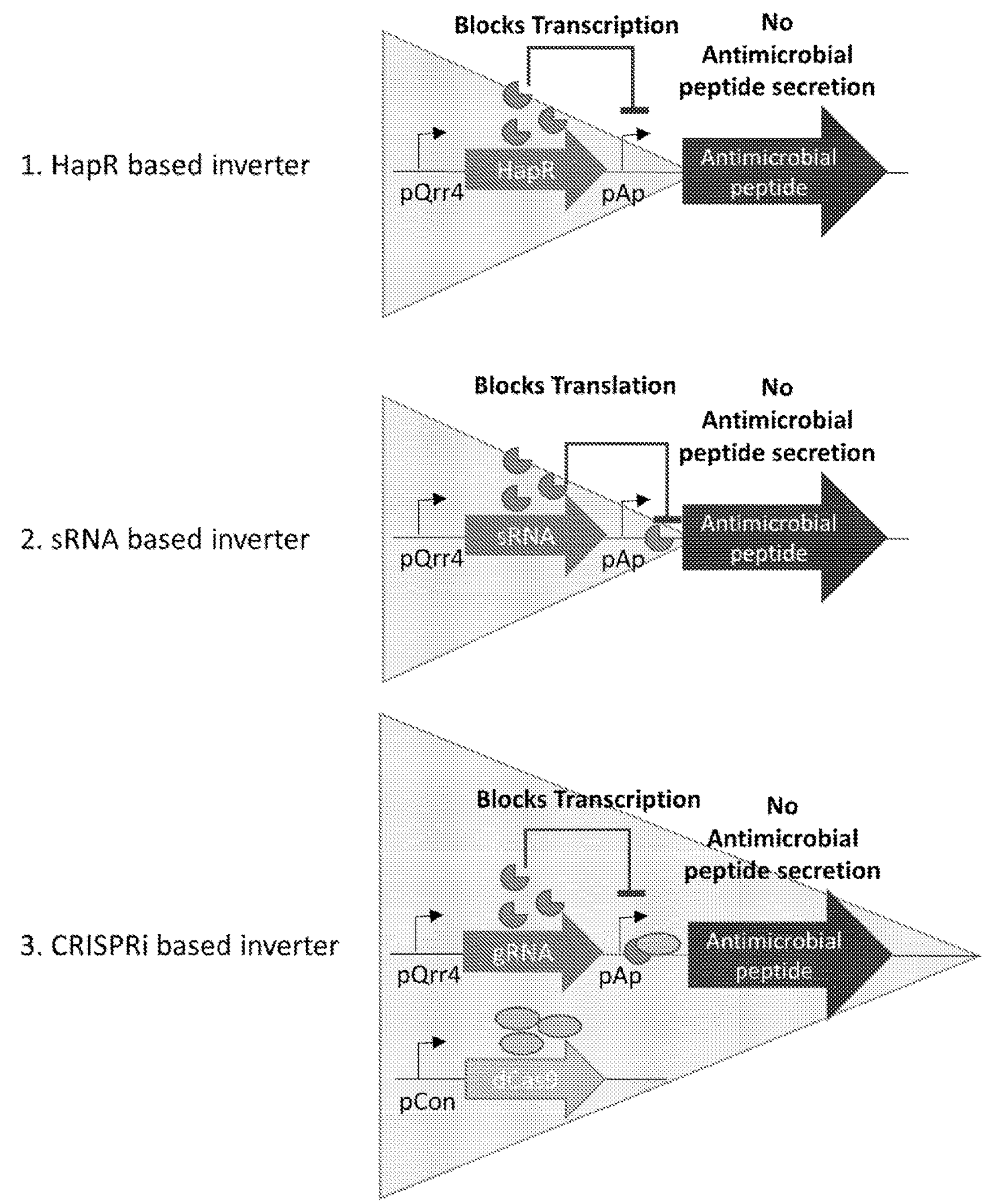

FIG. 2 Overview of different types of genetic inverters

Depicted are three different genetic inverters types

The first genetic inverter is based on a promoter-repressor pair as exemplified with the HapR repressor, which blocks transcription from the pAhpA promoter and hence of any antimicrobial peptide under control of the pAhpA promoter. The pAhpA promoter labelled pAp (promoter of Antibacterial peptide) is an example for a promoter driving the antimicrobial peptide.

The second genetic inverter is based on a sRNA. In this case, the genetic inverter sRNA binds to the mRNA of the antimicrobial peptide and this represses translation of the antimicrobial peptide.

The third genetic inverter is a CRISPRi based genetic inverter. It is based on the dCas9 protein and associated guide RNA (gRNA). These in tandem repress expression of any given promoter by blocking the transcription initiation.

Figure 3:
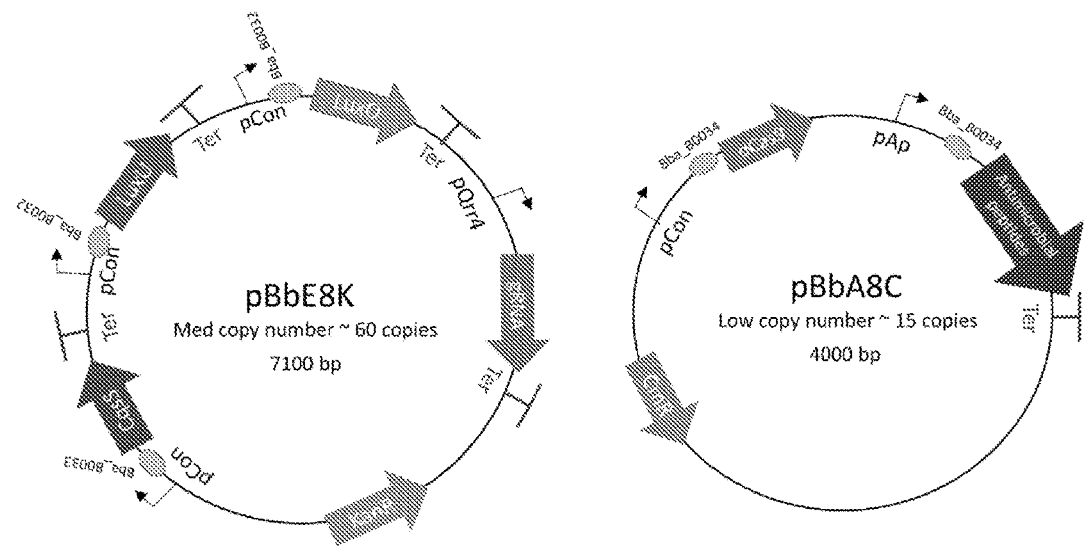

FIG. 3 Overview of plasmid maps of an exemplary recombinant expression system Shown is the plasmid design of an exemplary recombinant expression system according to the present invention. In this example a recombinant expression system comprising a CRISPRi based genetic inverter is depicted.

Figure 4:
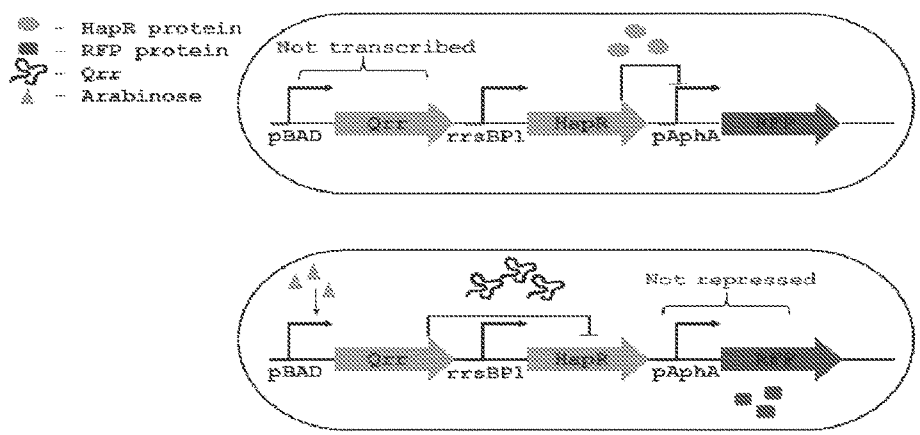

FIG. 4 Schematic overview of the working principle of a recombinant expression system comprising a promoter-repressor type genetic inverter, here exemplified with pAphA and HapR.

In order to characterize the pAhpA promoter—HapR repressor pair, a single plasmid, in which Red Fluorescent Protein (RFP) is expressed under control of the pAhpA promoter, was constructed. Using this system, the level of RFP fluorescence of the culture is controlled by addition of different levels of arabinose. When no arabinose is present, the pBAD promoter is not induced and no Qrr (sRNA preventing HapR translation) is produced, thereby allowing the expression of the HapR protein, which in turn represses the expression from the pAphA promoter. Therefore, no RFP is expressed in the absence of arabinose. As soon as the arabinose concentration exceeds a threshold level, HapR expression is inhibited, thereby allowing transcription from the pAphA promoter and thus RFP expression.

Figure 5:
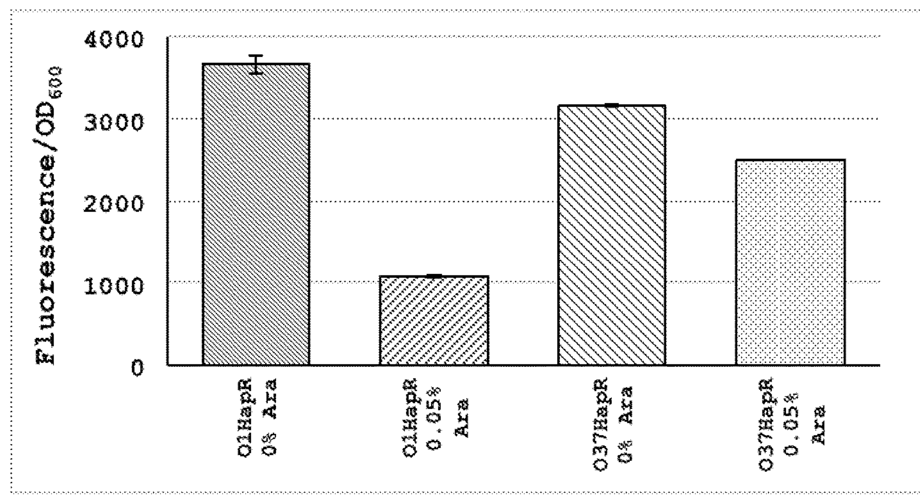

FIG. 5 Shown is a comparison of fluorescence levels of cultures expressing HapR following induction by arabinose and cultures not expressing HapR. HapRs coming from two different serotypes of *V. cholerae,* 01 and 037 strains, were compared.

Figure 6:
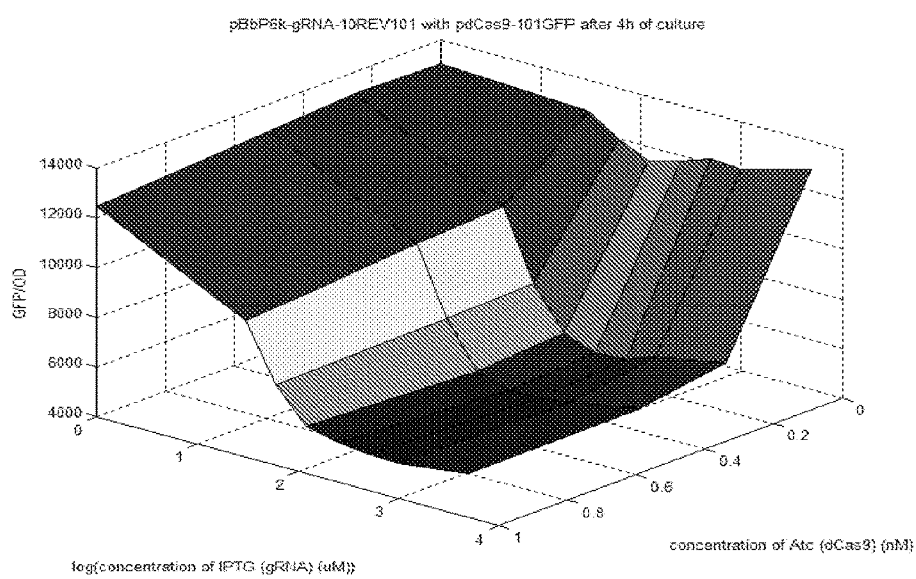

FIG. 6 Shown are differences in GFP expression level with different Atc and IPTG concentrations in the medium in cultures expressing a CRISPRi based genetic inverter. The genetic inverter, with which these results were generated, utilizes the CRISPRi system, in which the dCas9 (dead Cas9) protein in tandem with corresponding gRNA effectively represses expression from a promoter. Here the dCAS9 protein was under control of the ATc induced promoter and the gRNA under control of an IPTG induced promoter. The results demonstrate the CRIPSRi genetic inverter has a good noise to signal level ratio.

Figure 7:
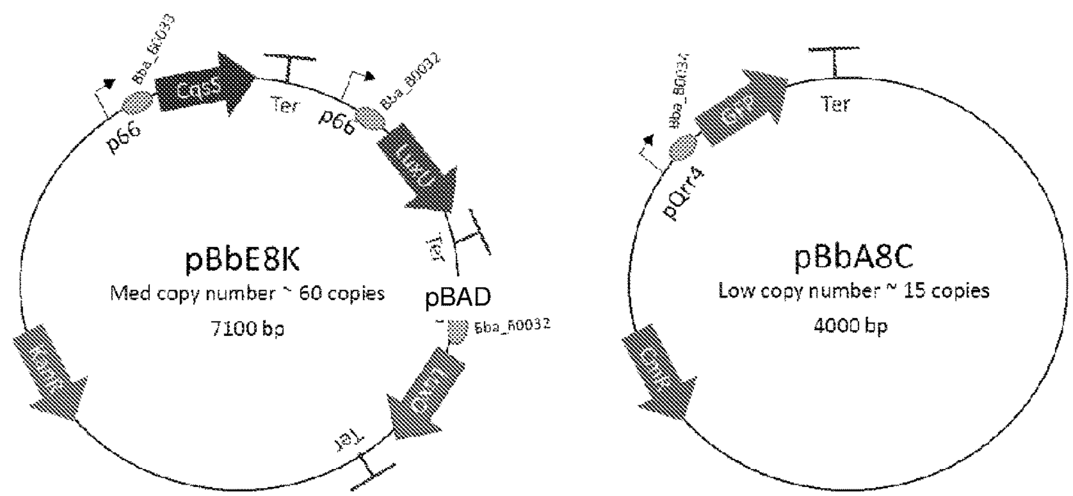

FIG. 7 Shown are the plasmid maps for an exemplary recombinant expression system comprising two nucleic acid constructs. The first nucleic acid construct, i.e. the first plasmid, harbours the CqsS, and LuxU as well as LuxO under pBAD promoter control, while GFP under pQrr4 promoter control is located on the second plasmid.

Figure 8:
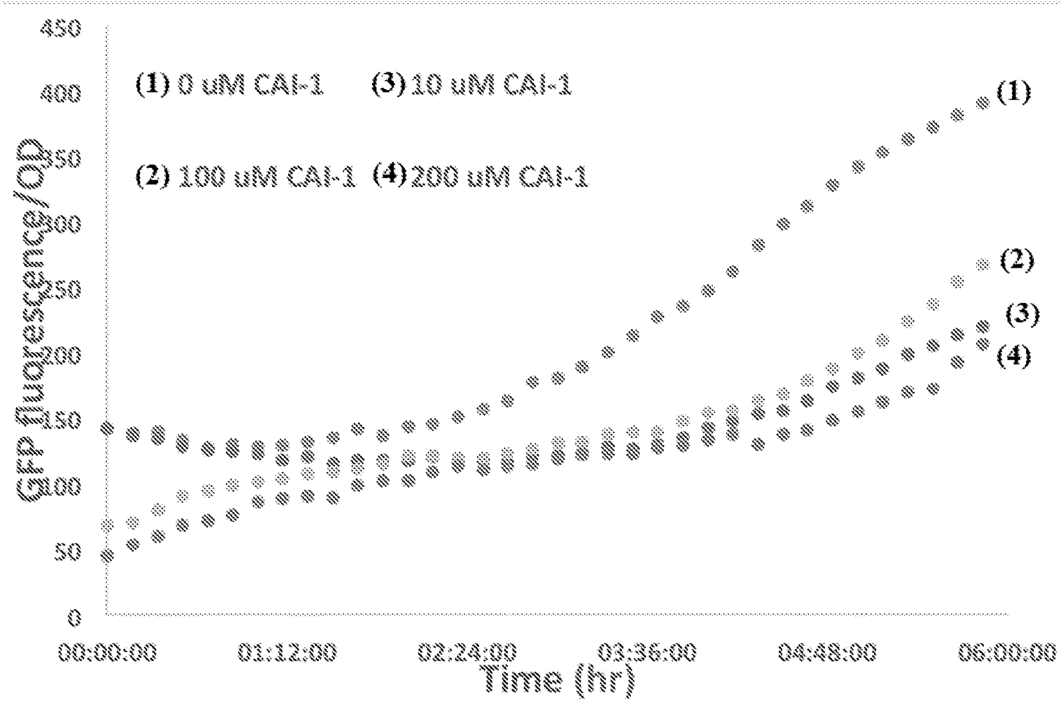
Figure 9:
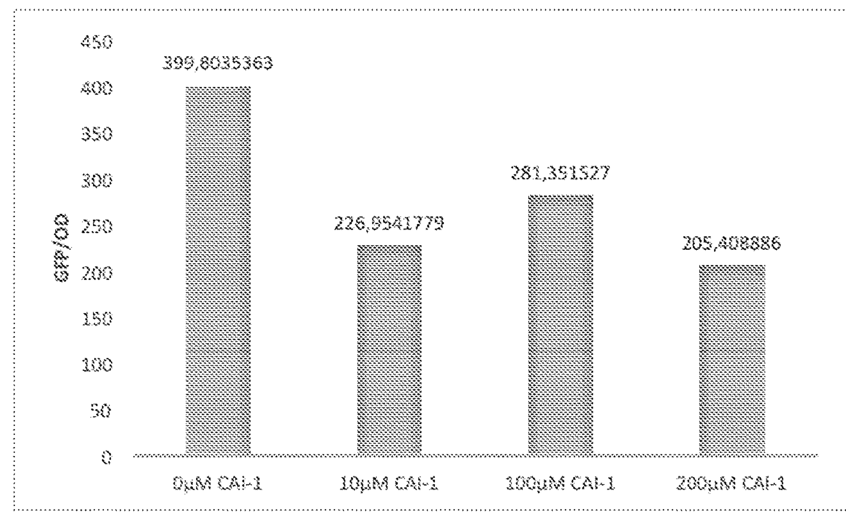

FIG. 8 and FIG. 9 show that depending on different CAI-1 concentrations GFP expression level varies, demonstrating that the recombinant expression system of FIG. 7 was able to sense the presence of CAI-1 marker molecule in the medium (the GFP fluorescence of the medium is a function of CAI-1 concentration). In the test construct the pBAD promoter drives LuxO. Hence, at high arabinose concentrations the pBAD promoter is induced and LuxO is expressed. When CAI-1 is added to the set-up, a drop in the GFP expression was observed. This is due to the downregulation of pQrr4 promoter by the CqsS cascade originating form *V. cholera*. In contrast, no alteration of GFP expression was observed when arabinose was present, but CAI-1 was absent. This shows the system is able to sense the presence of CAI-1 and represses the expression of GFP. The system is inducible by arabinose in order to add an additional level of control.

Figure 10:
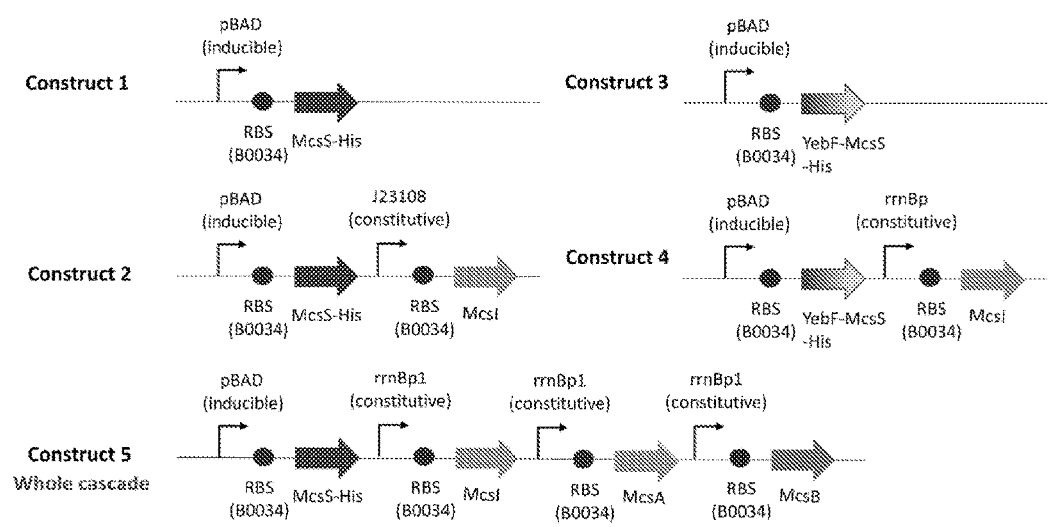

FIG. 10 An overview is given over five different plasmids constructs that were generated to evaluate the activity of Microcin S (mcsS) and Microcin immunity protein (mcsI) in *E. coli* Top10 cells.

Figure 11:
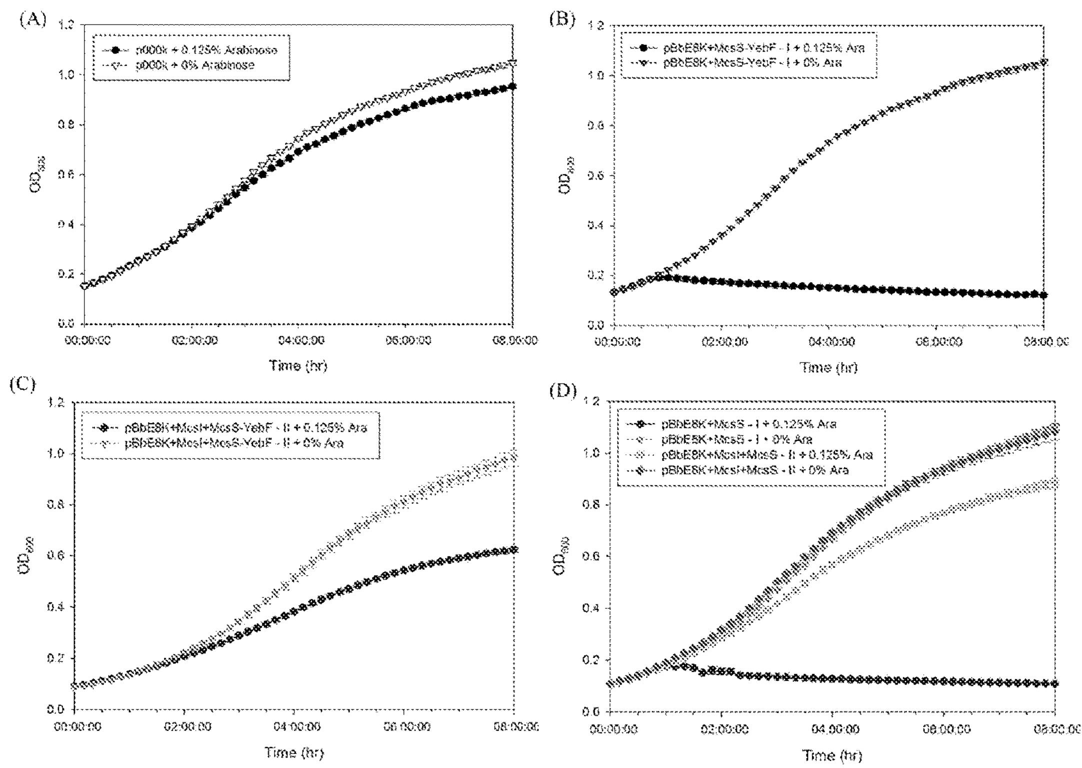

FIG. 11 Shown are growth curves of *E. coli* Top10 with different plasmids.

(A) p000k is an empty pBbE8K vector containing just the pBAD promoter without any coding sequence. Induction with L-Arabinose did not show significant impact on the growth of the cells. (B) pBbE8K+McsS-YebF is a vector containing McsS-YebF fusion peptide insert under control of the L-arabinose-induced araC pBAD activator-promoter. When induced with arabinose, a complete growth inhibition of the host cell (*E. coli* Top10) was observed, while uninduced cultures did not show any growth reduction. (C) pBbE8K+McsI+McsS-YebF is a vector containing McsS-YebF fusion peptide insert and McsI is produced constitutively under rrnB promoter. When induced, McsI (immunity protein) is able to restore the growth of *E. coli* by proteolysing the Microcin peptides. (D) pBbE8K+McsS is a vector containing the McsS insert under control of the L-arabinose-induced araC PBAD activator-promoter. Similarly, when induced with arabinose there is a complete growth inhibition of the host cell (*E. coli* Top10), while un-induced cultures did not show any growth reduction. Also the introduction of McsI gene restored the growth of *E. coli* cells.

Figure 12:
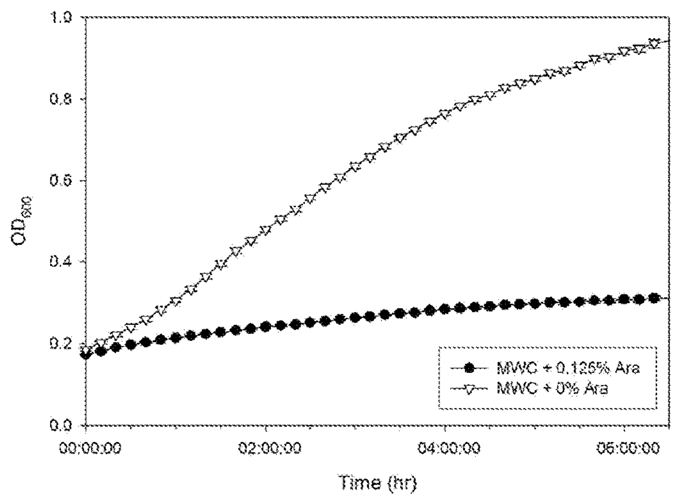

FIG. 12 Shown is the effect of Microcin S (construct 5 of FIG. 10) on *E. coli* cells.

Figure 13:
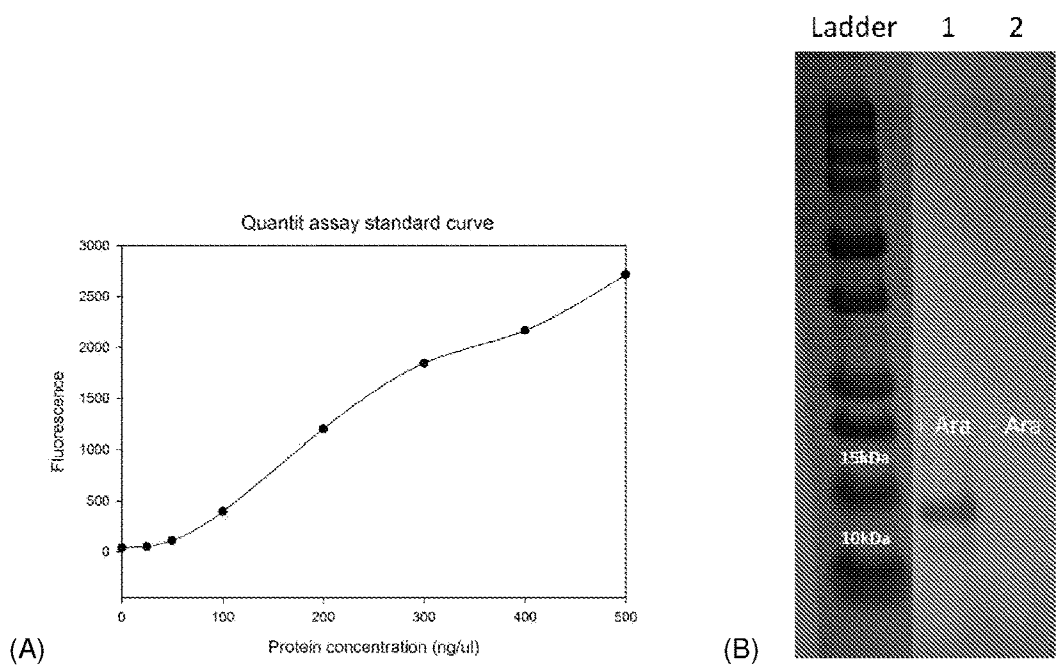

FIG. 13 Shown are the results of experiments related to expression and purification of Microcin S. (A) Quant-it assay standard curve, calibrated at measuring the fluorescence at 470/570 nm. (B) SDS PAGE results, Lane 1: Microcin S induced by 0.125% arabinose and Lane 2: Microcin S uninduced FIG. 14 Characterization of peptide the antimicrobial peptide CM11 (P3) expression in *E. coli* Top10. P3 after induction with 0.2% Ara reduces the growth of *E. coli* (bottom line) and uninduced sample grows normally (top line).

Figure 15:
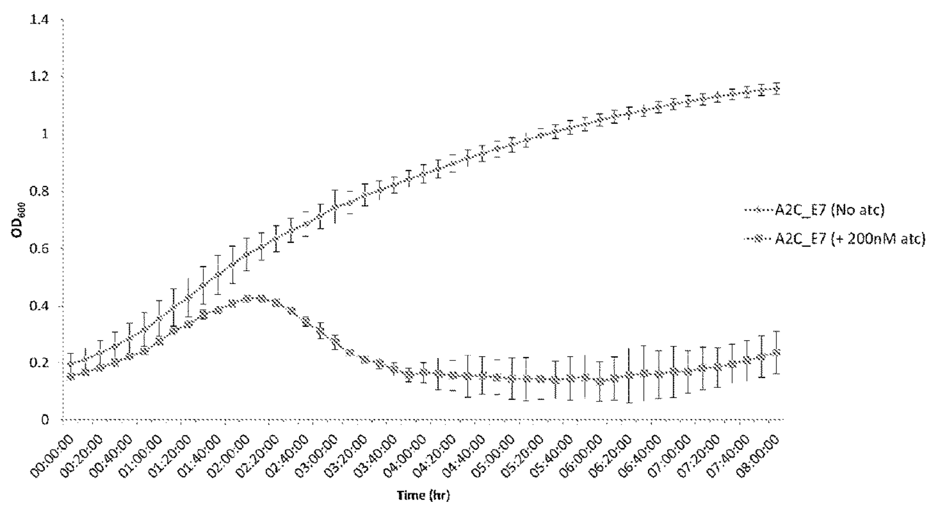

FIG. 15 Characterization of Lysis E7 expression in *E. coli*. Lysis E7 expressed when 200 nM of atc (anhydrotetracycline) is able to lyse *E. coli* within 4 hrs (bottom line). Uninduced sample grows normally (top line).

Figure 16:
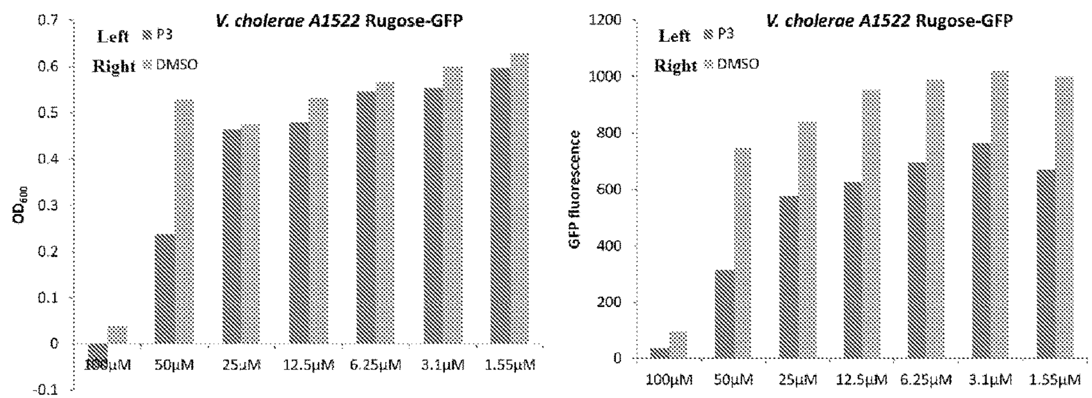

FIG. 16 MIC of the synthetic peptide CM11 (P3) against *V. cholerae* (A1522 Rugose-GFP). The target cells were effectively killed at an MIC of 50 μM. As a control only DMSO was used. As the target cells express GFP embedded into its chromosome, the GFP fluorescence (B) along with the absorbance (growth) (A) was monitored in this experiment.

Figure 17:
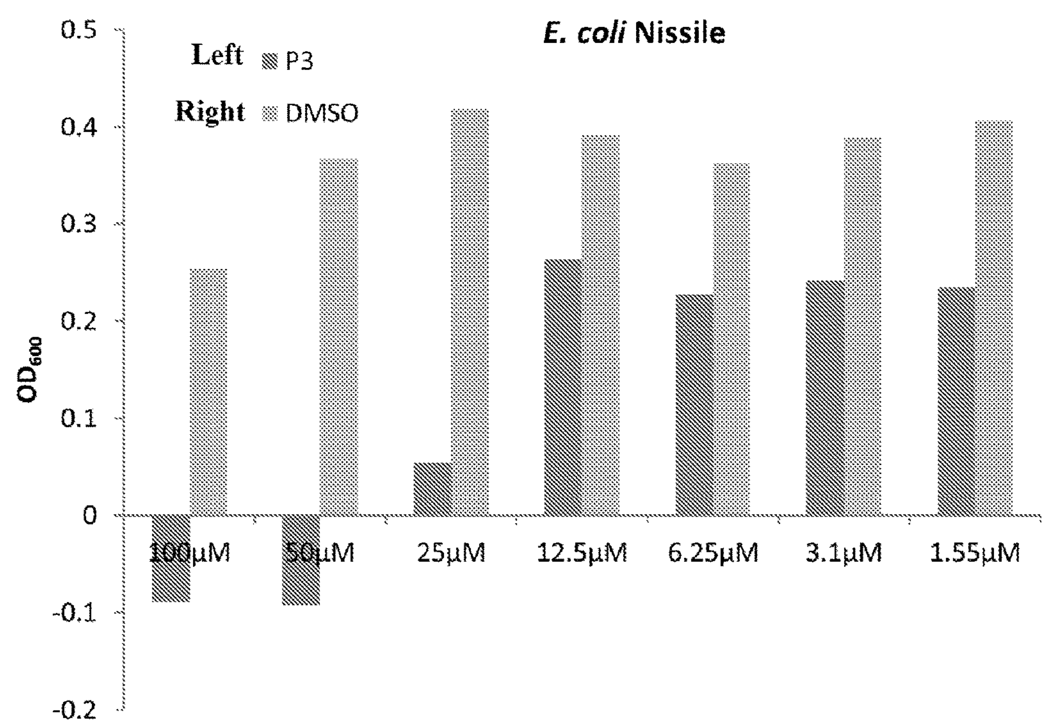

FIG. 17 MIC of the synthetic peptide CM11 (P3) against *E. coli* Nissile. The target cells were susceptible to the peptide at an MIC of 25 μM. As a control only DMSO was used.

DETAILED DESCRIPTION

A new recombinant expression systems designed for autonomous expression of at least one peptide is disclosed.

Thus, in a first aspect the invention relates to a recombinant expression system comprising at least:

(i) a first nucleotide sequence encoding for at least one protein of a quorum sensing system capable of detecting the presence, amount or both of a microorganism of interest by forming a complex with a marker molecule indicating the presence of said microorganism;

(ii) a second nucleotide sequence encoding for at least one antimicrobial peptide, wherein the at least one antimicrobial peptide is effective against the microorganism of interest detected by the at least one protein encoded by the first nucleotide sequence, (iii) a third nucleotide sequence encoding for a genetic inverter that inhibits expression of the second nucleotide sequence, wherein the genetic inverter is under control of an inducible promoter and wherein the inducible promoter is induced if the complex of the at least one protein encoded by the first nucleotide sequence and the marker molecule indicating the presence of said microorganism is below a threshold concentration and is not induced if the complex of the at least one protein encoded by the first nucleotide sequence and the marker molecule indicating the presence of said microorganism exceeds a threshold concentration "One or more", as used herein relates to at least 1 and includes 1, 2, 3, 4, 5, 6, 7, 8, 9 and more. Any function assigned to the "one or more" species may be achieved independently by each of the species or achieved by the combination of the more than one species.

The term "recombinant expression system" as used herein refers to a combination of an expression vector, its cloned nucleic acid, and optionally the host for the vector that provide a context to allow for the production of the sequence encoded by a nucleic acid at a high level in the host.

The recombinant expression system may be designed to operate in vitro or may be a cell based recombinant expression system. In a preferred embodiment, the recombinant expression system is a prokaryotic cell based system.

The term "nucleic acid construct" as used herein refers to a nucleic acid molecule that includes a given sequence. The nucleic acid may be DNA, RNA, DNA:RNA hybrids, PNA and the like, but preferably is DNA. The construct can be an expression vector for expression of a protein encoded by a recombinant gene carried by said vector, a plasmid, cosmid, or artificial chromosome. A preferred vector is a vector that can self-replicate and express a given nucleic acid sequence included therein.

Quorum sensing is the regulation of gene expression in response to fluctuations in cell-population density. Quorum sensing bacteria (Gram-positive and Gram-negative) produce and release chemical signal molecules called autoinducers that increase in concentration as a function of cell density. The detection of a minimal threshold stimulatory concentration of an autoinducer leads to an alteration in gene expression.

Thus, the protein of a quorum sensing system may be any protein of a quorum sensing signalling cascade capable of detecting the presence, amount or both of a microorganism of interest by forming a complex with a marker molecule indicating the presence of said microorganism.

As used herein the term "microorganism" is intended to include living cellular organisms, both unicellular and multicellular that are less than 5 mm in length, and include but are not limited to bacteria, fungi, archaea, protists, green algae, plankton, planarian, amoebas and yeasts, or spores formed by any of these.

The term "antimicrobial peptide" refers to a peptide that exhibits microbicidal or microbiostatic and/or bactericidal or bacteriostatic properties that enables the peptide to kill, destroy, inactivate, or neutralize a microorganism; or to prevent or reduce the growth, ability to survive, or propagation of a microorganism.

The term "genetic inverter" as used herein refers to a regulatory element that inhibits expression of the at least one antimicrobial peptide or the at least one detectable marker, thereby preventing that the at least one antimicrobial peptide is active in the absence of the microorganism of interest or that the at least one detectable marker can be detected in the absence of the microorganism of interest.

As used herein, the terms "promoter", "promoter element", and "promoter sequence" refer to a DNA sequence, which is capable of controlling the transcription of the nucleotide sequence into mRNA when the promoter is placed at the 5 end of (i.e., precedes) a nucleotide sequence. Thus, a promoter is typically located 5' (i.e., upstream) of a nucleotide sequence whose transcription into mRNA it controls, and provides a site for specific binding by RNA polymerase and for initiation of transcription.

The term "inducible promoter" as used herein refers to a promoter that can be regulated by the presence or absence of biotic or abiotic factors such as transcription factors. Thus, an inducible promoter can either be positively or negatively regulated. For instance an inducible promoter can mean a promoter that has low activity in the absence of an activator.

On the contrary, a promoter can have high activity in the absence of an agent, which negatively regulates the promoter.

In this regard it should be noted that in the inventive recombinant expression system the inducible promoter positively regulates the genetic inverter. Thus, the genetic inverter is expressed whenever the promoter is active and can then negatively regulate expression of the at least one antimicrobial peptide or the at least one detectable marker. In other words, the inducible promoter is downregulated upon presence of the complex formed by the at least one protein of a quorum sensing system capable of detecting the presence, amount or both of a microorganism of interest and the marker molecule indicating the presence of the microorganism of interest. Consequently, the genetic inverter is also downregulated and not expressed once this complex is present in sufficient quantities, which leads to expression of the at least one antimicrobial peptide or the at least one detectable marker.

The term "threshold" as used herein refers to the minimum level at which the complex of the at least one protein encoded by the first nucleotide sequence and the marker molecule indicating the presence of the microorganism of interest induces the inducible promoter.

The term "marker molecule" as used herein refers to any molecule that can form a complex with the at least one protein of a quorum sensing system encoded by the first nucleotide sequence.

In various embodiments of the recombinant expression system, the marker molecule is chosen from the group consisting of small molecules, lipids, phospholipids, amino acids, monoamines, peptide, proteins, glycoproteins, or gases.

The term "first nucleotide sequence", "second nucleotide sequence" etc., as used herein, relate to nucleic acid sequences that encode for one or more gene products of a given functionality. Accordingly, the first nucleotide sequence may comprise one or more genes with each of said genes encoding for a separate gene product. This applies similarly to other nucleotide sequences. All of these nucleotide sequences may comprise additional non-coding sequence stretches required for transcription and translation of the respective coding sequences.

Generally, the nucleic acid constructs may additionally comprise further regulatory elements, such as enhancers or silencers, all of which are well known to those skilled in the art.

Advantageously, this recombinant expression system is capable of autonomously regulating the expression of the at least one antimicrobial peptide. Thus, once the concentration of the complex of the at least one protein of a quorum sensing system and the marker molecule indicating the present of the microorganism of interest is exceeding a threshold concentration, the genetic inverter is inactivated and the at least one antimicrobial peptide is produced.

On the contrary, if the concentration of the complex of the at least one protein of a quorum sensing system and the marker molecule indicating the presence of the microorganism is below the threshold concentration, i.e., the microorganism of interest is not present or present in low amounts, the system autonomously represses production of the at least one antimicrobial peptide.

Moreover, the combination of inducible promoter and genetic inverter also allows for a very precise control of the expression of the at least one antimicrobial peptide.

Therefore, this recombinant expression system may be used as a preventative measure, since it will only produce the at least one antimicrobial peptide upon autonomous detection of the microorganism of interest.

In various embodiments of the recombinant expression system the genetic inverter (a) comprises a nucleotide sequence encoding a repressor molecule and a promoter repressed by the repressor, with said promoter controlling expression of the second nucleotide sequence, (b) comprises a nucleotide sequence encoding an sRNA specific for the mRNA encoded by the second nucleotide sequence or (c) is a CRISPRi system comprising a nucleotide sequence encoding for a gRNA sequence specific for the second nucleotide sequence and a nucleotide sequence encoding for dCas9 protein As demonstrated in FIGS. 6, 8 and 9 these genetic inverters allow a precise and reliable repression of the antimicrobial peptide when the concentration of the complex of the at least one protein of a quorum sensing system and the marker molecule indicating the presence of the microorganism of interest is below the threshold concentration.

By carefully choosing a suitable genetic inverter the recombinant expression system may be targeted to the specific needs of a given application, i.e. to targeting a variety of microorganisms.

In a suitable promoter-repressor pair the repressor inhibits transcription from the promoter of the at least one antimicrobial peptide or the at least one detectable marker. Hence, the promoter-repressor pair represses transcription of the at least one antimicrobial peptide or the at least one detectable marker.

Examples for promoter-repressor pairs are the pAhpA promoter and the HapR repressor, PhiF and pPhiF, LacI and pTac, TetR and pTetR and BetI with pBetI.

As used herein, the term "sRNA" refers to a short-length RNA (small RNA), which is usually 200 or less nucleotides in length, which is not translated into protein and which effectively inhibits the translation of a specific mRNA by complementary binding. Thus, an sRNA-based genetic inverter represses translation of the antimicrobial peptide.

A genetic inverter based on the CRISPRi system represses transcription of the antimicrobial peptide.

Based on the bacterial genetic immune system—CRISPR (clustered regularly interspaced palindromic repeats) pathway, the CRISPR interference (CRISPRi) technique is a genetic perturbation technique that allows for sequence-specific repression or activation of gene expression in prokaryotic and eukaryotic cells.

The CRISPRi system relies on the catalytically inactive Cas9 enzyme termed dCAS9. dCas9 is unable to cleave dsDNA but retains the ability to target and bind DNA. Targeting specificity is determined by complementary base-pairing of a single guide RNA (gRNA) to the genomic loci. The gRNA is a chimeric noncoding RNA that can be subdivided into three regions: a 20 nt base-pairing sequence, a 42 nt dCas9-binding hairpin and a 40 nt terminator. Taken together gRNA and dCas9 provide a minimum system for gene-specific regulation in any organism.

When designing a synthetic gRNA, only the 20 nt base-pairing sequence is modified from the overall template.

Moreover, tailoring of the recombinant expression system may also be achieved via altering the first nucleotide sequence encoding for at least one protein of a quorum sensing system capable of detecting the presence, amount or both of a microorganism of interest by forming a complex with a marker molecule indicating the presence of said microorganism. Via choosing a suitable protein of a quorum sensing system, it is possible to target a desired microorganism.

In one embodiment of the recombinant expression system the genetic inverter is a CRISPRi system, wherein the nucleotide sequence encoding for a gRNA sequence specific for the second nucleotide sequence is under control of the inducible promoter and the nucleotide sequence encoding for dCas9 is constitutively expressed.

As used herein the term "gRNA" refers to guided RNA, i.e. to a RNA, which is specific for the target DNA and can form a complex with dCas9 protein and bring dCas9 protein to the target DNA.

As demonstrated in FIG. 6 such a recombinant expression system allows a precise and reliable repression or expression, respectively, of the peptide or protein of interest.

In a preferred embodiment of such a recombinant expression system the promoter controlling the genetic inverter sequence is the Qrr4 promoter (SEQ ID NO 4).

In one embodiment of the recombinant expression system the detection mechanism of the first nucleotide sequence is based on the CqsS/CAI-1 quorum-sensing phosphorelay system of *V. cholerae.*

The mechanism of the *V. cholerae* CqsS/CAI-1 quorum-sensing phosphorelay system is as follows: CqsS is the CAI-1 receptor. At low cell density when CAI-1 concentration is below the detection limit, CqsS functions as a kinase. Following auto-phosphorylation at His194, the phosphoryl group is transferred to Asp618 on the CqsS receiver domain. The next transfer is to His58 on LuxU. LuxU, in turn, transfers the phosphoryl group to Asp47 on LuxO. Once phosphorylated, LuxO via binding to σ54 factor activates the transcription from the Qrr4 promoter (pQrr4). At high cell density CAI-1 accumulates, binds CqsS, and switches CqsS to a phosphatase. Phospho-flow is reversed and LuxO is dephosphorylated. Consequently, transcription from the Qrr4 promoter ceases.

It is preferred that the detection mechanism of the first nucleotide sequence is or comprises a heterologous detection system. This may help to avoid interference with cellular pathways of the host cell.

In one embodiment of the recombinant expression system the first nucleotide sequence encodes for the proteins of the (S)-3-hydroxytridecan-4-one (CAI-1) sensor module and thus comprises the nucleotide sequence encoding for the LuxO protein having the amino acid sequence as set forth in SEQ ID NO: 8, the nucleotide sequence encoding for the CqsS protein having the amino acid sequence as set forth in SEQ ID NO: 6 and the nucleotide sequence encoding for the LuxU protein having the amino acid sequence as set forth in SEQ ID NO: 7.

In various embodiments of the recombinant expression system the one or more antimicrobial peptide is selected from the group consisting of McsS (SEQ ID NO 9), G12.21 (SEQ ID NO 10), G14.15 (SEQ ID NO 11), CM11 (SEQ ID NO 12), CM15 (SEQ ID NO 13) and Magainin 2 (SEQ ID NO 14), L1 (SEQ ID NO 30), L2 (SEQ ID NO 31), B1 (SEQ ID NO 32) and CP1 (SEQ ID NO 33).

In one embodiment of the recombinant expression system the antimicrobial peptide is Microcin S (SEQ ID NO 9).

In various embodiments of the recombinant expression system the antimicrobial peptide is fused to a secretory peptide.

In one embodiment of the recombinant expression system the at least one antimicrobial peptide is fused to the YebF (SEQ ID NO 15) secretory peptide. Other possible secretory peptides include, FlgM (SEQ ID NO 34) or lysis E7 (SEQ ID NO 35).

In a preferred embodiment of the recombinant expression system the at least one antimicrobial peptide McsS (SEQ ID NO 9) is fused to a YebF peptide (McsS-YebF, SEQ ID NO 16).

In a further aspect the invention relates to a recombinant cell comprising a recombinant expression system as described above.

Such an embodiment has the advantage the cell can be used as preventative measure against a microorganism of interest and autonomously initiates expression of an antimicrobial peptide, if the concentration of this microorganism exceeds a threshold level.

In various embodiments of this aspect of the invention the recombinant cell is a genetically engineered prokaryotic cell.

In various embodiments the prokaryotic cell is a probiotic bacteria.

Such an embodiment has the advantage that the probiotic bacteria can be manipulated and grown easily and efficiently even in large-scale fermenters, thereby leading to substantial cost advantages.

Moreover, engineered probiotic bacteria could be ingested in a similar manner as how existing probiotic bacteria are taken (e.g. yoghurts, drinks, capsules, dried forms, etc.), which can be made available in very affordable forms, readily distributed when necessary and taken without the need for medical expertise/devices (e.g. presence of doctors, use of needles, etc.). These are important factors for use in developing countries where infections such as cholera are most prevalent.

In various embodiments the prokaryotic cell is an *Escherichia coli* cell.

In one embodiment the *Escherichia coli* cell is a probiotic *E. coli* Nissle cell.

These recombinant cells have the advantage that they can actively sense and kill the microorganism of interest such as a human pathogen, e.g. *V. cholerae.*

Advantageously, the inventive recombinant expression system allows the secretion of the antimicrobial peptide. Thus, there is no negative effect on the host cell, as it would be the case, if the host cell has to be destroyed or lyzed in order to release the at least one antimicrobial peptide. This leads to a higher production of the antimicrobial peptide, since the host cell can continuously produce the antimicrobial peptide until the concentration of the complex of the at least one protein of a quorum sensing system and the marker molecule indicating the present of said microorganism is below the threshold level.

However, it is also possible that the at least one antimicrobial peptide is released through lysis of the recombinant cell.

In a further aspect, the present invention relates to a method of sensing and killing pathogenic microorganisms, the method comprising contacting the recombinant cell described above with the pathogenic microorganism.

This method has the advantage that it is designed to protect from suffering from microorganisms such as *Vibrio cholerae*. It serves as a preventative measure, since it will only produce the antimicrobial peptide upon detection of the microorganisms such as *V. cholerae*. It could potentially be used as a drug.

One embodiment of the method of sensing and killing pathogenic microorganisms comprises administering the recombinant cell to a subject.

In one embodiment of the method of sensing and killing pathogenic microorganisms the pathogenic microorganism is a human pathogen.

In a preferred embodiment of the method of sensing and killing pathogenic microorganisms the pathogenic microorganism is selected from the group consisting of *Pseudomonas aeruginosa, Clostridium difficile, Escherichia coli, Helicobacter pylori, Salmonella, Vibrio cholerae* and *Yersinia.*

In a further aspect, the present invention relates to the use of a recombinant expression comprising at least:

(i) a first nucleotide sequence encoding for at least one protein of a quorum sensing system capable of detecting the presence, amount or both of a microorganism of interest by forming a complex with a marker molecule indicating the presence of said microorganism;

(ii) a second nucleotide sequence encoding for at least one detectable marker, (iii) a third nucleotide sequence encoding for a genetic inverter that inhibits expression of the second nucleotide sequence, wherein the genetic inverter is under control of an inducible promoter and wherein the inducible promoter is induced if the complex of the at least one protein encoded by the first nucleotide sequence and the marker molecule indicating the presence of said microorganism is below a threshold concentration and is not induced if the complex of the at least one protein encoded by the first nucleotide sequence and the marker molecule indicating the presence of said microorganism exceeds a threshold concentration, for detection of at least one type of microorganism.

Such a system has the advantage that it can autonomously detect the presence of a microorganism of interest.

As used herein the term "detectable marker" refers to any organic chemical compound, peptide, protein or DNA or RNA molecule capable of giving rise to a detectable signal that indicates the presence of microorganism of interest. A "detectable signal" is a signal that is either visible to the naked eye or detectable (readable) with the aid of an instrument, such as a spectrophotometer. Accordingly, detection may be by spectroscopic, photochemical, biochemical, immunochemical, or chemical means.

Detection peptides are well known in the art for detection in immunoblotting, ELISA and other such assay techniques.

Other embodiments are within the following claims and non-limiting examples. It is to be understood that these examples are for illustrative purposes only and are not to be construed to limit the scope of the present invention.

EXAMPLES

Example 1: Construction of a Recombinant Expression System

A recombinant expression system was constructed, comprising pAphA, HapR and the Qrr4. These components are part of the quorum sensing mechanism in *V. cholerae.*

In detail, the usability of pAphA as constitutive promoter for RFP expression was investigated and pAphA repressibility by HapR and its efficacy were elucidated.

Differences in ability to repress pAphA by HapRs coming from two different serotypes of *V. cholerae*—the 01 and 037 strains—were found. These are due to a single point mutation in HarpR from 037 strain (see FIG. 5).

To characterize the performance of the recombinant expression system, a single plasmid was generated, in which Red Fluorescent Protein (RFP) is expressed under control of the pAhpA promoter. Via addition of arabinose the levels of HapR (SEQ IS NO 38) in the cells could be regulated. This means that by addition of different levels of arabinose into the medium the RFP fluorescence of the culture could be changed. The working principle of the system is shown in FIG. 4.

In the next step, a double plasmid system, with the CqsS (SEQ ID NO 6), LuxU (SEQ ID NO 7) and LuxO (SEQ ID NO 8) genes expressed on one plasmid and GFP (SEQ ID NO) under pQrr4 promoter (SEQ ID NO 19) on another was generated. The working principle is shown in FIG. 7. Thus, this system comprises the CAI-1 sensor module, in which phosphorylated LuxO activates the Qrr4 promoter. In the test construct the pBAD promoter drives LuxO, which is inducible by arabinose. Hence, only at high arabinose concentrations LuxO is expressed.

The results shown in FIGS. 8 and 9 demonstrate that the system was able to sense the presence of different concentrations of CAI-1 in the medium (the GFP fluorescence of the medium is a function of CAI-1 concentration). In other words, the system changes its fluorescence with different concentrations of CAI-1.

Example 2: Construction of a Genetic CRISPR Based Genetic Inverter

In this experiment it was determined, which part of the CRISPR system should be put under Qrr4 promoter control. To achieve this, the Cas9 protein (SEQ ID NO 39) was controlled by the ATc inducible promoter (SEQ ID NO 18) and the gRNA (SEQ ID NO 29) was put under control of an IPTG inducible promoter. The results of FIG. 6 show that the dCas9 protein (SEQ ID NO 39) in tandem with the corresponding gRNA effectively represses expression from a promoter. The biggest advantage of this system is its versatility, as it can be used to represses nearly any desired promoter.

Example 3: Characterization of Antimicrobial Peptides

In this experiment the antimicrobial activities of Microcin S (SEQ ID NO 9), which is produced by probiotic *E. coli* G3/10 and synthetic peptides against *V. cholerae* and susceptible *E. coli* strains were investigated. Five synthetic peptides shown previously to have activity against *V. cholerae* and pathogenic *E. coli* were chosen. Two of the peptides G12.21 (SEQ ID NO 10) and G14.15 (SEQ ID NO 11) are granulysin based and where shown to effectively control the growth of *V. cholerae* both in vitro and in vivo (Da Silva et al. 2008). Similarly, two cationic peptides—CM15 (SEQ ID NO 13) and CM11 (SEQ ID NO 12)—which show inhibitory activity against *V. cholerae* and other pathogenic bacteria such as *P. aeruginosa, S. aureus, A. baumannii* and *E. coli* (Moghaddam et al. 2012) were tested. Moreover, the broad spectrum peptide, Magainin 2 (SEQ ID NO 14), which has a good killing efficiency on *V. cholerae* and pathogenic *E. coli* (Yaraksa et al. 2014) was chosen.

Moreover, for the secretion of Microcin S out of the producing strain, the YebF fusion protein (SEQ ID NO 15) was studied. YebF is a small, soluble endogenous protein, which can carry fusion proteins in their active states into the medium as early as 3 h after induced expression.

To evaluate the activity of Microcin S (mcsS) and Microcin immunity protein (mcsI) in *E. coli* Top10 cells five different plasmids were constructed (FIG. 10). Growth curves of *E. coli* harbouring different plasmids are shown in FIG. 11. In order to directly demonstrate Microcin S activity against a susceptible *E. coli* strain (Top10), mcsS and mcsS-YebF were cloned separately into the pBbE8K vector resulting in the plasmids pBbE8K+McsS-YebF-I and pBbE8K+McsS-I (Table 1).

TABLE 1

Sequences of the synthetic parts used for the expression of sensor proteins

| | |
|---|---|
| BBa_B0032 (RBS) | SEQ ID NO 23 |
| BBa_B0033 (RBS) | SEQ ID NO 24 |
| BBa_B0034 (RBS) | SEQ ID NO 25 |
| BBa_B0015 (Terminator) | SEQ ID NO 26 |
| p66 (Promoter) | SEQ ID NO 22 |

Moreover, also the effect of Microcin immunity protein (mcsI) in the presence of Microcin S was studied. For this, the mcsI gene was introduced into the pBbE8K+McsS-YebF-I and pBbE8K+McsS-I plasmids resulting in pBbE8K+McsI+McsS-YebF-II and pBbE8K+McsI+McsS-II, respectively. In these constructs, mcsS expression is controlled by an araC pBAD activator-promoter (SEQ ID NO), rendering Microcin S expression inducible by L-arabinose. In contrast, mcsI expression is constitutively ON when using the rrnB promoter (SEQ ID NO 28).

When *E coli* Top10 growing in liquid culture after being transformed with pBbE8K+McsS-YebF-I or pBbE8K+McsS-I were treated with 0.125% v/v L-arabinose the OD600 reading was significantly reduced compared to the un-induced and control cultures (p000k—vector devoid of any CDS) (FIG. 11).

When *E coli* Top10 cells growing in liquid culture after being transformed with pBbE8K+McsI+McsS-YebF-II or pBbE8K+McsI+McsS-II were treated with 0.125% v/v L-arabinose the OD600 reading was restored significantly compared to the un-induced and control cultures (p000k—vector devoid of any CDS) (FIG. 11). This clearly shows that mcsI immunity protein is acting as protease and the proteolysis of the Microcin S peptides restores growth in the host cell.

Therefore, the fusion of McsS to YebF does not hinder the Microcin S activity, as its killing potential is similar to that of McsS alone. Moreover, the McsI immunity protein supports the survival of the host cells, by protecting the host cells from the Microcin S activity, while the secreted Microcin S can target potential pathogens such as *V. cholerae.*

Furthermore, also the effect of Microcin whole cascade in *E. coli* Top10 growing in liquid culture with 0.125% arabinose and without arabinose after being transformed with construct 5 of FIG. 12 was studied. It was found that *E coli* expressing Microcin S had reduced OD600 readings after induction with arabinose (dark circles) compared to readings of the uninduced (unfilled inverted triangles) *E. coli* cells (FIG. 12). This shows that Microcin S is effective in killing of *E. coli.*

In addition, the Microcin S peptide was purified to test its efficacy on *V. cholerae* and *E. coli*. For protein purification *E. coli* Top10 harbouring construct 1 of FIG. 10 were grown in 250 ml culture until 0.8 OD600 and Microcin S expression was fully induced by 0.125% arabinose for 2 hrs at 37° C. Subsequently, the cells were pelleted by centrifugation at 4000 g for 20 min and lysed using a sonicator. Purification of Microcin S was carried out using Qiagen Ni-NTA fast start kit. The eluate was dialysed using Slide-A-Lyzer dialysis cassette and a 2 KDa cutoff (Life Technologies) for 4 hrs in 1×PBS. The dialysed samples were concentrated by ultra filtration using a molecular mass cutoff membrane (Amicon Ultra-15 Centrifugal Filter Unit, Millipore). As the estimated size of the protein is approximately 12 kDa, the first concentration was done using a 30 kDa cutoff membrane where the flow-through was collected and subsequently passed through a 3 kDa cutoff membrane. The resulting retentate was collected and the concentration was quantified using Quant-IT protein assay kit (Life Technologies).

Figure 14:
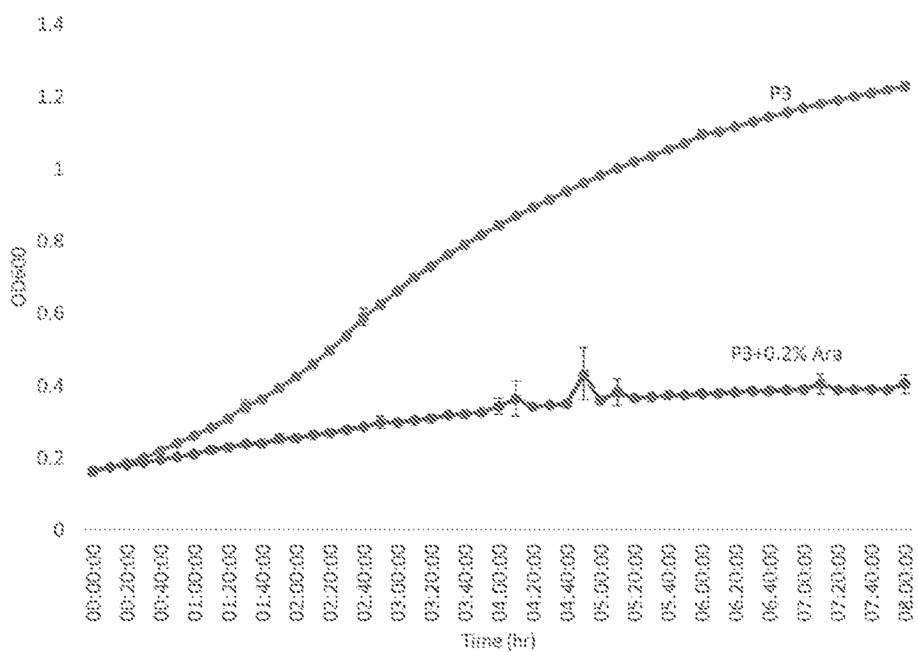

The induced sample expressed has Microcin S (FIG. 13B) and the fluorescence reading from the Quant-it assay was 1135, which was close to a concentration of 200 ng/μl, calculated from the standard curve (FIG. 13A). No Microcin S was found in the uninduced sample as demonstrated by the SDS PAGE results (FIG. 13B) and the fluorescence reading was 652. After the presence of Microcin S was confirmed from the purified sample, a microbroth dilution assay was carried out to measure the minimum inhibitory concentration of purified Microcin S on *V. cholerae* and *E. coli.* 50 μl of each sample were serially diluted in 50 μl of LB broth in a 96 well plate. 50 μl of bacteria culture (*E. coli* wt/*V. cholerae*) were added to the diluted samples. The total volume was 100 μl with a runtime for 4 hrs followed by a check of the OD and the killing efficiency. Minimal inhibition of both *V. cholerae* and *E. coli* was observed at 100 ng/μl of Microcin S (FIG. 14). From these experiments it is clearly evident that purified Microcin S has inhibitory activity (FIG. 15) against *V. cholerae* and *E. coli.*

Moreover, also the killing efficiency of the synthetic peptides listed in Table 2 below was studied.

TABLE 2

Synthetic peptides.

| | Synthetic peptide |
|---|---|
| 1 | G12.21 |
| 2 | G14.15 |
| 3 | CM11 |
| 4 | CM15 |
| 5 | Magainin 2 |

For example, in the case of CM11 (P3) the P3 gene was cloned under the arabinose promoter (pBAD) in the pBbE8K vector resulting in the pBbE8K+P3 plasmid. In other words, P3 expression in this construct is controlled by an araC PBAD activator-promoter, rendering P3 expression inducible by L-arabinose. When, *E coli* Top10 growing in liquid culture after being transformed with pBbE8K+P3, were treated with 0.2% v/v L-arabinose the OD600 reduced significantly compared to the un-induced sample (FIG. 14). Thus, this directly demonstrates P3 activity against a susceptible *E. coli* strain.

Moreover, a minimum inhibitory concentration (MIC) assay was conducted using CM11 (P3). The medium used for the broth microdilution test was LB Broth and the cells were *V. cholera* A1522-Rugose-GFP and *E. coli* Nissile strains. Overnight cultures were transferred into 5 ml of LB and were grown at 37° C. for 2-3 h. To approximate the density of 0.5 McFarland standard, this suspension with the inoculum concentration of 108 colony forming units (CFU/ml) was then diluted to 106 CFU/ml with the LB broth. Peptide P3 stock solution of 1000 μg/ml was prepared using DMSO. Serial two-fold dilutions of the peptide (P3) with the following concentration (2-100 μg/ml) were prepared with LB broth and placed in 96-well microtiter plates and the lowest concentration inhibiting visible growth after 18-20 h at 37° C. was recorded as MIC (see FIGS. 16 and 17).

In addition, in order to characterize the lysis activity in *E. coli*, the lysis E7 gene was cloned under the tetracycline promoter (pTet) in the pBbA2C vector resulting in the pBbA2C+E7 plasmid. Hence, E7 expression is controlled by an pTet activator-promoter, rendering E7 expression inducible by anhydrotetracycline (atc). When *E coli* Top10 growing in liquid culture after being transformed with pBbA2C+E7, were treated with 200 nM anhydrotetracycline (atc) the OD600 reduced significantly due to the lysis compared to the un-induced sample (FIG. 15).

Furthermore, gentamicin resistance was introduced into kanamycin resistant *E. coli* cells (E8K_aacC1) in order to be able to co-culture them with the target *V. cholera* cells. Our target strain has gentamicin resistance embedded into its chromosome.

When tested with gentamicin and kanamycin *E. coli* Top10 harbouring E8K_aacC1 were able to grow normally, while the control strain *E. coli* (harbouring E8K_109), which possesses only kanamycin resistance, was unable to grow in gentamicin (results not shown).

By "comprising" it is meant including, but not limited to, whatever follows the word "comprising". Thus, use of the term "comprising" indicates that the listed elements are required or mandatory, but that other elements are optional and may or may not be present.

By "consisting of is meant including, and limited to, whatever follows the phrase "consisting of. Thus, the phrase "consisting of indicates that the listed elements are required or mandatory, and that no other elements may be present.

By "about" in relation to a given numerical value, such as for temperature and period of time, it is meant to include numerical values within 10% of the specified value.

The inventions illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Sequence Listing

The sequences mentioned throughout the specification refer to the following:

| | Name | Sequence | SEQ ID NO |
|---|---|---|---|
| 1 | pAphA | ggtcacaactttgtggccttt<br>tgttttacatttttttcattat<br>tgagaataatgtcagtttttc<br>gactaatcagcatatttgtat<br>tccactttatgcttattattt<br>agatatactacgttccctctg<br>tgataagtaatgtaaagc | 1 |

-continued

| | Name | Sequence | SEQ ID NO |
|---|---|---|---|
| 2 | HapR | atggacgcatcaatcgaaaaa<br>cgccctcgaactcggctatcg<br>cctcaaaaacgcaaactacaa<br>ctgatggaaatcgcgttggaa<br>gtgtttgctaaacgcggcatt<br>ggtcgtggtggtcacgcagat<br>attgccgagattgcgcaagtc<br>tccgttgcaacagtgttcaac<br>tacttcccaactcgtgaagac<br>ttggttgacgatgtgctgaat<br>tttgtggttcgtcagtactcc<br>aacttcttgaccgatcacatc<br>gatcttgatttggatgtgaaa<br>accaacctacaaactctgtgc<br>aaagagatggtgaaattggcg<br>atgaccgattgtcactggctc<br>aaagtctggtttgagtggagt<br>gcttcaacccgtgacgaagtt<br>tggccactgtttgtttccacc<br>aaccgaactaaccaactgctg<br>atcagaaacatgtttatgaaa<br>gcgatggagcgtggcgaattg<br>tgtgagaaacacgatgtcgat<br>aacatggccagcctgttccac<br>ggcatcttctactccatcttc<br>ttacaagtgaaccgtttaggt<br>gaacaagaagcagtgtataag<br>ttggccgatagctacctcaat<br>atgctgtgtatctataagaac<br>ta | 2 |
| 3 | CRISPR based genetic inverter gRNA | gacagctagcattgtaccaag<br>ttttagagctagaaatagcaa<br>gttaaaataaggctagtccgt<br>tatcaacttgaaaaagtggca<br>ccgagtcggtgcttttttt | 3 |
| 4 | pQrr4 | agttggcacgtaatctgcatt<br>tattagattg | 4 |
| 5 | dCas9 | Atggataagaaatactcaata<br>ggcttagctatcggcacaaat<br>agcgtcggatgggcggtgatc<br>actgatgaatataaggttccg<br>tctaaaaagttcaaggttctg<br>ggaaatacagaccgccacagt<br>atcaaaaaaaatcttataggg<br>gctcttttatttgacagtgga<br>gagacagcggaagcgactcgt<br>ctcaaacggacagctcgtaga<br>aggtatacacgtcggaagaat<br>cgtatttgttatctacaggag<br>atttttcaaatgagatggcg<br>aaagtagatgatagtttcttt<br>catcgacttgaagagtctttt<br>ttggtggaagaagacaagaag<br>catgaacgtcatcctattttt<br>ggaaatatagtagatgaagtt<br>gcttatcatgagaaatatcca<br>actatctatcatctgcgaaaa<br>aaattggtagattctactgat<br>aaagcggatttgcgcttaatc<br>tatttggccttagcgcatatg<br>attaagtttcgtggtcatttt<br>ttgattgagggagatttaaat<br>cctgataatagtgatgtggac<br>aaactatttatccagttggta<br>caaacctacaatcaattattt<br>gaagaaaaccctattaacgca<br>agtggagtagatgctaaagcg<br>attctttctgcacgattgagt<br>aaatcaagacgattagaaaat<br>ctcattgctcagctccccggt<br>gagaagaaaaatggcttattt<br>gggaatctcattgctttgtca<br>ttgggtttgacccctaatttt | 5 |

-continued

| Name | Sequence | SEQ ID NO |
|---|---|---|
| | aaatcaaattttgatttggca | |
| | gaagatgctaaattacagctt | |
| | tcaaaagatacttacgatgat | |
| | gatttagataatttattggcg | |
| | caaattggagatcaatatgct | |
| | gatttgtttttggcagctaag | |
| | aatttatcagatgctatttta | |
| | ctttcagatatcctaagagta | |
| | aatactgaaataactaaggct | |
| | cccctatcagcttcaatgatt | |
| | aaacgctacgatgaacatcat | |
| | caagacttgactcttttaaaa | |
| | gctttagttcgacaacaactt | |
| | ccagaaaagtataaagaaatc | |
| | ttttttgatcaatcaaaaaac | |
| | ggatatgcaggttatattgat | |
| | gggggagctagccaagaagaa | |
| | ttttataaatttatcaaacca | |
| | attttagaaaaaatggatggt | |
| | actgaggaattattggtgaaa | |
| | ctaaatcgtgaagatttgctg | |
| | cgcaagcaacggacctttgac | |
| | aacggctctattccccatcaa | |
| | attcacttgggtgagctgcat | |
| | gctattttgagaagacaagaa | |
| | gacttttatccatttttaaaa | |
| | gacaatcgtgagaagattgaa | |
| | aaaatcttgacttttcgaatt | |
| | ccttattatgttggtccattg | |
| | gcgcgtggcaatagtcgtttt | |
| | gcatggatgactcggaagtct | |
| | gaagaaacaattaccccatgg | |
| | aattttgaagaagttgtcgat | |
| | aaaggtgcttcagctcaatca | |
| | tttattgaacgcatgacaaac | |
| | tttgataaaaatcttccaaat | |
| | gaaaaagtactaccaaaacat | |
| | agtttgctttatgagtatttt | |
| | acggtttataacgaattgaca | |
| | aaggtcaaatatgttactgaa | |
| | ggaatgcgaaaaccagcattt | |
| | ctttcaggtgaacagaagaaa | |
| | gccattgttgatttactcttc | |
| | aaaacaaatcgaaaagtaacc | |
| | gttaagcaattaaaagaagat | |
| | tatttcaaaaaaatagaatgt | |
| | tttgatagtgttgaaatttca | |
| | ggagttgaagatagatttaat | |
| | gcttcattaggtacctaccat | |
| | gatttgctaaaaattattaaa | |
| | gataaagatttttttggataat | |
| | gaagaaaatgaagatatctta | |
| | gaggatattgttttaacattg | |
| | accttatttgaagatagggag | |
| | atgattgaggaaagacttaaa | |
| | acatatgctcacctctttgat | |
| | gataaggtgatgaaacagctt | |
| | aaacgtcgccgttatactggt | |
| | tggggacgtttgtctcgaaaa | |
| | ttgattaatggtattagggat | |
| | aagcaatctggcaaaacaata | |
| | ttagatttttttgaaatcagat | |
| | ggttttgccaatcgcaatttt | |
| | atgcagctgatccatgatgat | |
| | agtttgacatttaaagaagac | |
| | attcaaaaagcacaagtgtct | |
| | ggacaaggcgatagtttacat | |
| | gaacatattgcaaatttagct | |
| | ggtagccctgctattaaaaaa | |
| | ggtattttacagactgtaaaa | |
| | gttgttgatgaattggtcaaa | |
| | gtaatggggcggcataagcca | |
| | gaaaatatcgttattgaaatg | |
| | gcacgtgaaaatcagacaact | |
| | caaaagggccagaaaaattcg | |
| | cgagagcgtatgaaacgaatc | |

-continued

| Name | Sequence | SEQ ID NO |
|---|---|---|
| | gaagaaggtatcaaagaatta | |
| | ggaagtcagattcttaaagag | |
| | catcctgttgaaaatactcaa | |
| | ttgcaaaatgaaaagctctat | |
| | ctctattatctccaaaatgga | |
| | agagacatgtatgtggaccaa | |
| | gaattagatattaatcgttta | |
| | agtgattatgatgtcgatgcc | |
| | attgttccacaaagtttcctt | |
| | aaagacgattcaatagacaat | |
| | aaggtcttaacgcgttctgat | |
| | aaaaatcgtggtaaatcggat | |
| | aacgttccaagtgaagaagta | |
| | gtcaaaaagatgaaaaactat | |
| | tggagacaacttctaaacgcc | |
| | aagttaatcactcaacgtaag | |
| | tttgataatttaacgaaagct | |
| | gaacgtggaggtttgagtgaa | |
| | cttgataaagctggttttatc | |
| | aaacgccaattggttgaaact | |
| | cgccaaatcactaagcatgtg | |
| | gcacaaattttggatagtcgc | |
| | atgaatactaaatacgatgaa | |
| | aatgataaacttattcgagag | |
| | gttaaagtgattaccttaaaa | |
| | tctaaattagtttctgacttc | |
| | cgaaaagatttccaattctat | |
| | aaagtacgtgagattaacaat | |
| | taccatcatgcccatgatgcg | |
| | tatctaaatgccgtcgttgga | |
| | actgctttgattaagaaatat | |
| | ccaaaacttgaatcggagttt | |
| | gtctatggtgattataaagtt | |
| | tatgatgttcgtaaaatgatt | |
| | gctaagtctgagcaagaaata | |
| | ggcaaagcaaccgcaaaatat | |
| | ttcttttactctaatatcatg | |
| | aacttcttcaaaacagaaatt | |
| | acacttgcaaatggagagatt | |
| | cgcaaacgccctctaatcgaa | |
| | actaatggggaaactggagaa | |
| | attgtctgggataaagggcga | |
| | gattttgccacagtgcgcaaa | |
| | gtattgtccatgccccaagtc | |
| | aatattgtcaagaaaacagaa | |
| | gtacagacaggcggattctcc | |
| | aaggagtcaattttaccaaaa | |
| | agaaattcggacaagcttatt | |
| | gctcgtaaaaaagactgggat | |
| | ccaaaaaaatatggtggtttt | |
| | gatagtccaacggtagcttat | |
| | tcagtcctagtggttgctaag | |
| | gtggaaaaagggaaatcgaag | |
| | aagttaaaatccgttaaagag | |
| | ttactagggatcacaattatg | |
| | gaaagaagttcctttgaaaaa | |
| | aatccgattgactttttagaa | |
| | gctaaaggatataaggaagtt | |
| | aaaaaagacttaatcattaaa | |
| | ctacctaaatatagtcttttt | |
| | gagttagaaaacggtcgtaaa | |
| | cggatgctggctagtgccgga | |
| | gaattacaaaaaggaaatgag | |
| | ctggctctgccaagcaaatat | |
| | gtgaatttttatatttagct | |
| | agtcattatgaaaagttgaag | |
| | ggtagtccagaagataacgaa | |
| | caaaaacaattgtttgtggag | |
| | cagcataagcattatttagat | |
| | gagattattgagcaaatcagt | |
| | gaattttctaagcgtgttatt | |
| | ttagcagatgccaatttagat | |
| | aaagttcttagtgcatataac | |
| | aaacatagagacaaaccaata | |
| | cgtgaacaagcagaaaatatt | |
| | attcatttatttacgttgacg | |

-continued

| | Name | Sequence | SEQ ID NO |
|---|---|---|---|
| | | aatcttggagctcccgctgct tttaaatattttgatacaaca attgatcgtaaacgatatacg tctacaaaagaagttttagat gccactcttatccatcaatcc atcactggtctttatgaaaca cgcattgatttgagtcagcta ggaggtgactaa | |
| 6 | CqsS | MIVSMDVIKRVYQYAEPNLSL VGWMGMLGFPAYYFIWEYWFP QSYENLGLRCAAAVLFGGLVF RDSMPKKWQRYMPGYFLFTIG FCLPFFFAFMMLMNDWSTIWA MSFMASIFLHILLVHDTRVMA LQALFSVLVAYLAVYGLTDFH PTTLIEWQYIPIFLFTYVFGN LCFFRNQISHETKVSIAKTFG AGIAHEMRNPLSALKTSIDVV RTMIPKPQTAAHTDYSLDAQE LDLLHOILNEADDVIYSGNNA IDLLLTSIDENRVSPASFKKH SVVDVIEKAVKTFPYKNAADQ HSVELEVHQPFDFFGSDTLLT YALFNLLKNAFYYQKEHFSVC ISIEQTSEHNLIRVRDNGVGI APEMLEDIFRDFYTFGKNGSY GLGLPFCRKVMSAFGGTIRCA SQQGQWTEFVLSFPRYDSDTV NEIKTELLKTKSLIYIGSNQA IVRELNQLAVEDEFGFTAISA QQAVRRQDYEFEFDLILLDLD DATAQGELLPKLEGTLSFAEG CIGYVYDPGKTYAVNINRYLR IQPISIHSILRKPRKIIERLL FEQESLSMNRNVIPLQKSRHE RRILVVDDNQSIRTFTAILLE QQGYEVVQANDGSEVLKHMES QNIDLVLMDIEMPNVGGLEAT RLIRNSEHEYKNIPIIGYTGD NSPKTLALVQTSGMNDFIVKP ADRDVLLNKVAAWV | 6 |
| 7 | LuxU | MREWINQSKIDLLAKEIGEEN VPILVNIFLGELNDYQSKLVS DTVADKLGYLKEISHALKSSA ASFGADRLCAKAVELDSRAKS GEMMDISLEVEHMLELLKQTH QCYSDLVH | 7 |
| 8 | LuxO | MVEDTASVAALYRSYLTPLDI DINIVGTGRDAIESIGRREPD LILLDLRLPDMTGMDVLYAVK EKSPDVPIVFMTAHGSIDTAV EAMRHGAQDFLIKPCEADRLR VTVNNAIRKASKLKNDVDNKN QNYQGFIGSSQTMQAVYRTID SAASSKASIFITGESGTGKEV CAEAIHAASKRGDKPFIAINC AAIPKDLIESELFGHVKGAFT GAATERQGAAEAADGGTLFLD ELCEMDLDLQTKLLRFIQTGT FQKVGSSKMKSVDVRFVCATN RDPWKEVQEGRFREDLYYRLY VIPLHLPPLRARGDDVIEIAY SLLGFMSKEEGKDFVRLSAEV VERFRQYEWPGNVRQLQNVLR NVVVLNEGREITLDMLPPPLN QMSAPINRALPLAHENKVSVH EIFPLWMTEKQAIEQAIEACD GNIPRAATYLDVSPSTIYRKL QTWNEKVKEKEKER | 8 |
| 9 | Microcin S peptide | MSNIRELSFDEIALVSGGNAN SNYEGGGSRSRNTGARNSLGR NAPTHIYSDPSTVKCANAVFS GMVGGAIKGGPVGMTRGTIGG AVIGQCLSGGGNGNGGGNRAG SSNCSGSNVGGTCSR | 9 |
| 10 | G12.21 | rrvsrrpmrryrsrrprrlv | 10 |
| 11 | G14.15 | grsrwrrvsrrfmrr | 11 |
| 12 | CM11 | WKLFKKILKVL-NH2 | 12 |
| 13 | CM15 | KWKLFKKIGAVLKVL-NH2 | 13 |
| 14 | Magainin 2 | GIGKFLHSAKKFGKAFVGEIM NS | 14 |
| 15 | YebF | MKKRGAFLGLLLVSACASVFA ANNETSKSVTFPKCEDLDAAG IAASVKRDYQQNRVARWADDQ KIVGQADPVAWVSLQDIQGKD DKWSVPLTVRGKSADIHYQVS VDCKAGMAEYQRR | 15 |
| 16 | McsS-YebF | MSNIRELSFDEIALVSGGNAN SNYEGGGSRSRNTGARNSLGR NAPTHIYSDPSTVKCANAVFS GMVGGAIKGGPVGMTRGTIGG AVIGQCLSGGGNGNGGGNRAG SSNCSGSNVGGTCSKKRGAFL GLLLVSACASVFAANNETSKS VTFPKCEDLDAAGIAASVKRD YQQNRVARWADDQKIVGQADP VAWVSLQDIQGKDDKWSVPLT VRGKSADIHYQVSVDCKAGMA EYQRR | 16 |
| 17 | IPTG inducible promoter | aattgtgagcggataacaatt gacattgtgagcggataacaa gatactgagcac | 17 |
| 18 | ATc inducible promoter | cctaattttgttgacactct atcgttgatagagttatttta ccactccctatcagtgataga gaaaa | 18 |
| 19 | GFP | MRKGEELFTGVVPILVELDGD VNGHKFSVSGEGEGDATYGKL TLKFICTTGKLPVPWPTLVTT FGYGVQCFARYPDHMKQHDFF KSAMPEGYVQERTIFFKDDGN YKTRAEVKFEGDTLVNRIELK GIDFKEDGNILGHKLEYNYNS HNVYIMADKQKNGIKVNFKIR HNIEDGSVQLADHYQQNTPIG DGPVLLPDNHYLSTQSALSKD PNEKRDHMVLLEFVTAAGITH GMDELYK | 19 |
| 20 | RFP | MASSEDVIKEFMRFKVRMEGS VNGHEFEIEGEGEGRPYEGTQ TAKLKVTKGGPLPFAWDILSP QFQYGSKAYVKHPADIPDYLK LSFPEGFKWERVMNFEDGGVV TVTQDSSLQDGEFIYKVKLRG TNFPSDGPVMQKKTMGWEAST ERMYPEDGALKGEIKMRLKLK DGGHYDAEVKTTYMAKKPVQL PGAYKTDIKLDITSHNEDYTI VEQYERAEGRHSTGA | 20 |
| 21 | pBAD | ctgacgctttttatcgcaact ctctactgt | 21 |
| 22 | p66 | gtatatattaaaacattcttg acatcttgaaacaaatatgat ataatagcaatatat | 22 |

-continued

| | Name | Sequence | SEQ ID NO |
|---|---|---|---|
| 23 | Bba_B0032 | tctagagtcacacaggaaagtactag | 23 |
| 24 | Bba_B0033 | tctagagtcacacaggactactag | 24 |
| 25 | Bba_B0034 | aaagaggagaaa | 25 |
| 26 | BBa_B0015 | aggatctccaggcatcaaataaaacgaaaggctcagtcgaaagactgggcctttcgttttatctgttgtttgtcggtgaacgctctctactagagtcacactggctcaccttcgggtgggcctttctgcgtttata | 26 |
| 27 | araC pBAD promoter | ttatgacaacttgacggctacatcattcactttttcttcacaaccggcacggaactcgctcgggctggccccggtgcattttttaaatacccgcgagaaatagagttgatcgtcaaaaccaacattgcgaccgacggtggcgataggcatccgggtggtgctcaaaagcagcttcgcctggctgatacgttggtcctcgcgccagcttaagacgctaatccctaactgctggcggaaaagatgtgacagacgcgacggcgacaagcaaacatgctgtgcgacgctggcgatatcaaaattgctgtctgccaggtgatcgctgatgtactgacaagcctcgcgtacccgattatccatcggtggatggagcgactcgttaatcgcttccatgcgccgcagtaacaattgctcaagcagatttatcgccagcagctccgaatagcgcccttccccttgcccggcgttaatgatttgcccaaacaggtcgctgaaatgcggctggtgcgcttcatccgggcgaaagaaccccgtattggcaaatattgacggccagttaagccattcatgccagtaggcgcgcggacgaaagtaaacccactggtgataccattcgcgagcctccggatgacgaccgtagtgatgaatctctcctggcgggaacagcaaaatatcacccggtcggcaaacaaattctcgtccctgatttttcaccaccccctgaccgcgaatggtgagattgagaatataacctttcattcccagcggtcggtcgataaaaaaatcgagataaccgttggcctcaatcggcgttaaacccgccaccagatgggcattaaacgagtatcccggcagcaggggatcattttgcgcttcagccat | 27 |
| 28 | rrsBP1 promoter | ttgtcaggccggaataactccctataat | 28 |
| 29 | Genetic inverter sRNA (Qrr4) | gacccttctaagccgagggtcacctagccaactgacgttgttagtgaacaccattgttcacacttatagacggccaatcacacttcttgtggttggcctttttttt | 29 |
| 30 | L1 | NGVQPKY | 30 |
| 31 | L2 | NAGSLLSGWG | 31 |
| 32 | B1 | LIAGLAANFLPKLFCKITK | 32 |

-continued

| | Name | Sequence | SEQ ID NO |
|---|---|---|---|
| 33 | CP1 | SWLSKTAKKLENSAKKRISEGIAIAIQGGPR | 33 |
| 34 | FIgM | ATGAGTATTGATCGCACTTCGCCTCTGAAGCCTGTAAGCACCGTTCAACCGCGCGAAACCACTGACGCGCCGGTAACGAACAGCCGGGCGGCAAAAACAACCGCCTCCACCAGCACCAGTGTGACGTTAAGCGACGCGCAAGCAAAACTGATGCAACCCGGCAGCAGTGATATCAATCTTGAACGTGTCGAAGCGTTAAAACTGGCGATTCGTAACGGTGAACTAAAAATGGACACCGGCAAAATTGCCGATGCGCTGATCAACGAAGCGCAGCAAGACTTGCAGAGTAAC | 34 |
| 35 | Lysis E7 | atgaaaaaaataacagggattattttattgcttcttgcagccattattcttgctgcatgtcaggcaaactatatccgtgatgttcagggcgggacagtatcaccgtcgtcaactgctgaactgaccggagtggaaacgcagtaa | 35 |
| 36 | aacC1 | ATGTTACGCAGCAGCAACGATGTTACGCAGCAGGGCAGTCGCCCTAAAACAAAGTTAGGTGGCTCAAGTATGGGCATCATTCGCACATGTAGGCTCGGCCCTGACCAAGTCAAATCCATGAGGGCTGCTCTTGATCTTTTCGGTCGTGAGTTCGGAGACGTAGCCACCTACTCCCAACATCAGCCGGACTCCGATTACCTCGGGAACTTGCTCCGTAGTAAGACATTCATCGCGCTTGCTGCCTTCGACCAAGAAGCGGTTGTTGGCGCTCTCGCGGCTTACGTTCTGCCAAAGTTTGAGCAGGCGCGTAGTGAGATCTATATCTATGATCTCGCAGTCTCCGGCGAGCACCGGAGGCAAG3GCATTGCCACCGCGCTCATCAATCTCCTCAAGCATGAGGCCAACGCGCTTGGTGCTTATGTGATCTACGTGCAAGCAGATTACGGTGACGATCCCGCAGTGGCTCTCTATACAAAGTTGGGCATACGGGAAGAAGTGATGCACTTTGATATCGACCCAAGTACCGCCACCTAA | 36 |
| 37 | CM11 (P3) | tggaaactgTTTAAAAAAATTCTGAAAGTGCTGAACCAT | 37 |
| 38 | HapR Protein | MDASIEKRPRTRLSPQKRKLQLMEIALEVFAKRGIGRGGHADIAEIAQVSVATVFNYFPTREDLVDDVLNFVVRQYSNFLTDHIDLDLDVKTNLQTLCKEMVKLAMTDCHWLKVWFEWSASTRDEVWPLFVSTNRTNQLLIRNMFMKAMERGELCEKHDVDNMASLFHGIFYSIFLQVNRLGEQEAVYKLADSYLNMLCIYKN | 38 |
| 39 | dCas9 protein | MDKKYSIGLAIGTNSVGWAVITDEYKVPSKKFKVLGNTDRHSIKKNLIGALLFDSGETAEATRLKRTARRRYTRRKNRICYLQEIFSNEMAKVDDSFFHRLEESFLVEEDKKHERHPIFGNIVDEVAYHEKYPTIYHLRKKLVDSTDKADLRLIYLALAHMIKFRGHF | 39 |

-continued

| Name | Sequence | SEQ ID NO |
|---|---|---|
| | LIEGDLNPDNSDVDKLFIQLV | |
| | QTYNQLFEENPINASGVDAKA | |
| | ILSARLSKSRRLENLIAQLPG | |
| | EKKNGLFGNLIALSLGLTPNF | |
| | KSNFDLAEDAKLQLSKDTYDD | |
| | DLDNLLAQIGDQYADLFLAAK | |
| | NLSDAILLSDILRVNTEITKA | |
| | PLSASMIKRYDEHHQDLTLLK | |
| | ALVRQQLPEKYKEIFFDQSKN | |
| | GYAGYIDGGASQEEFYKFIKP | |
| | ILEKMDGTEELLVKLNREDLL | |
| | RKQRTFDNGSIPHQIHLGELH | |
| | AILRRQEDFYPFLKDNREKIE | |
| | KILTFRIPYYVGPLARGNSRF | |
| | AWMTRKSEETITPWNFEEVVD | |
| | KGASAQSFIERMTNFDKNLPN | |
| | EKVLPKHSLLYEYFTVYNELT | |
| | KVKYVTEGMRKPAFLSGEQKK | |
| | AIVDLLFKTNRKVTVKQLKED | |
| | YFKKIECFDSVEISGVEDRFN | |
| | ASLGTYHDLLKIIKDKDFLDN | |
| | EENEDILEDIVLTLTLFEDRE | |
| | MIEERLKTYAHLFDDKVMKQL | |
| | KRRRYTGWGRLSRKLINGIRD | |
| | KQSGKTILDFLKSDGFANRNF | |
| | MQLIHDDSLTFKEDIQKAQVS | |
| | GQGDSLHEHIANLAGSPAIKK | |
| | GILQTVKVVDELVKVMGRHKP | |
| | ENIVIEMARENQTTQKGQKNS | |
| | RERMKRIEEGIKELGSQILKE | |
| | HPVENTQLQNEKLYLYYLQNG | |
| | RDMYVDQELDINRLSDYDVDA | |
| | IVPQSFLKDDSIDNKVLTRSD | |
| | KNRGKSDNVPSEEVVKKMKNY | |
| | WRQLLNAKLITQRKFDNLTKA | |
| | ERGGLSELDKAGFIKRQLVET | |
| | RQITKHVAQILDSRMNTKYDE | |
| | NDKLIREVKVITLKSKLVSDF | |
| | RKDFQFYKVREINNYHHAHDA | |
| | YLNAVVGTALIKKYPKLESEF | |
| | VYGDYKVYDVRKMIAKSEQEI | |
| | GKATAKYFFYSNIMNFFKTEI | |
| | TLANGEIRKRPLIETNGETGE | |
| | IVWDKGRDFATVRKVLSMPQV | |
| | NIVKKTEVQTGGFSKESILPK | |
| | RNSDKLIARKKDWDPKKYGGF | |
| | DSPTVAYSVLVVAKVEKGKSK | |
| | KLKSVKELLGITIMERSSFEK | |
| | NPIDFLEAKGYKEVKKDLIIK | |
| | LPKYSLFELENGRKRMLASAG | |
| | ELQKGNELALPSKYVNFLYLA | |
| | SHYEKLKGSPEDNEQKQLFVE | |
| | QHKHYLDEIIEQISEFSKRVI | |
| | LADANLDKVLSAYNKHRDKPI | |
| | REQAENIIHLFTLTNLGAPAA | |
| | FKYFDTTIDRKRYTSTKEVLD | |
| | ATLIHQSITGLYETRIDLSQL | |
| | GGD | |

REFERENCES

Alanis A J (2005) Resistance to antibiotics: are we in the post antibiotic era? Arch Med Res, 36:697-705

Culligan et al. (2009) Probiotics and gastrointestinal disease: successes, problems and future prospects. Gut Pathogens, 1:19

Moghaddam M M, Abolhassani F, Babavalian H, Mirnejad R, Azizi Barjini K, Amani J. Comparison of in vitro antimicrobial activities of two cationic peptides CM15 and CM11 against five pathogenic bacteria: *Pseudomonas aeruginosa, Staphylococcus aureus, Vibrio cholerae, Acinetobacter baumannii*, and *Escherichia coli*. Probiotics & Antimicro Prot. 2012 Jun. 1; 4(2):133-9.

Sack D A, Sack R B, Chaignat C L. (2006) Getting serious about cholera. N Engl J Med. 355(7):649-51.

Sinclair D, Abba K, Zaman K, Qadri F, Graves P M (2011). "Oral vaccines for preventing cholera". Cochrane Database Syst Rev (3): CD008603

Yaraksa N, Anunthawan T, Theansungnoen T, Daduang S, Araki T, Dhiravisit A, et al. Design and synthesis of cationic antimicrobial peptide based on Leucrocin I sequence, antimicrobial peptide from crocodile (*Crocodylus siamensis*) white blood cell extracts. The Journal of antibiotics. 2014 March; 67(3):205-12.

The invention claimed is:

1. A recombinant expression system comprising at least:

(i) a first nucleotide sequence encoding for at least one protein of a quorum sensing system capable of detecting the presence, amount or both of a microorganism of interest by forming a complex with a marker molecule indicating the presence of said microorganism, wherein the quorum sensing system of the first nucleotide sequence is based on the CqsS/CAI-1 quorum-sensing phosphorelay system of *V. cholerae;*

(ii) a second nucleotide sequence encoding for at least one antimicrobial peptide, wherein the at least one antimicrobial peptide is effective against the microorganism of interest detected by the at least one protein encoded by the first nucleotide sequence, wherein the one or more antimicrobial peptide(s) is selected from the group consisting of Microcin S (McsS, SEQ ID NO 9), CM11 (SEQ ID NO 12), CM15 (SEQ ID NO 13) and Magainin 2 (SEQ ID NO 14);

(iii) a third nucleotide sequence encoding for a genetic inverter that inhibits expression of the second nucleotide sequence, wherein the genetic inverter is under control of an inducible promoter;

wherein the inducible promoter is induced, if the complex of the at least one protein encoded by the first nucleotide sequence and the marker molecule indicating the presence of said microorganism is below a threshold concentration and is not induced, if the complex of the at least one protein encoded by the first nucleotide sequence and the marker molecule indicating the presence of said microorganism exceeds a threshold concentration; and wherein the inducible promoter controlling the genetic inverter is the Qrr4 promoter (SEQ ID NO 4).

2. The recombinant expression system according to claim 1, wherein the genetic inverter (a) comprises a nucleotide sequence encoding a repressor molecule and a promoter repressed by the repressor, with said promoter controlling expression of the second nucleotide sequence, (b) comprises a nucleotide sequence encoding an sRNA specific for the mRNA encoded by the second nucleotide sequence or (c) is a CRISPRi system comprising a nucleotide sequence encoding for a gRNA sequence specific for the second nucleotide sequence and a nucleotide sequence encoding for dCas9 protein.

3. The recombinant expression system according to claim 1, wherein the genetic inverter is a CRISPRi system, wherein the nucleotide sequence encoding for a gRNA sequence specific for the second nucleotide sequence is under control of the inducible promoter and the nucleotide sequence encoding for dCas9 is constitutively expressed.

4. The recombinant expression system according to claim 1, wherein the first nucleotide sequence encodes for the proteins of the (S)-3-hydroxytridecan-4- one (CAI-1) sensor module and thus comprises the nucleotide sequence encoding for the LuxO protein having the amino acid sequence as set forth in SEQ ID NO: 8, the nucleotide sequence encoding for the CqsS protein having the amino acid sequence as set forth in SEQ ID NO: 6 and the nucleotide sequence encoding for the LuxU protein having the amino acid sequence as set forth in SEQ ID NO: 7.

5. The recombinant expression system according to claim 1, wherein the antimicrobial peptide is fused to a secretory peptide.

6. The recombinant expression system according to claim 1, wherein the antimicrobial peptide is fused to the YebF (SEQ ID NO 15) secretory peptide.

7. The recombinant expression system according to claim 6, wherein the antimicrobial peptide McsS (SEQ ID NO 9) is fused to the YebF peptide (McsS-YebF, SEQ ID NO 16).

8. A recombinant cell comprising a recombinant expression system that comprises at least:

(i) a first nucleotide sequence encoding for at least one protein of a quorum sensing system capable of detecting the presence, amount or both of a microorganism of interest by forming a complex with a marker molecule indicating the presence of said microorganism, wherein the quorum sensing system of the first nucleotide sequence is based on the CqsS/CAI-1 quorum-sensing phosphorelay system of *V. cholerae;*

(ii) a second nucleotide sequence encoding for at least one antimicrobial peptide, wherein the at least one antimicrobial peptide is effective against the microorganism of interest detected by the at least one protein encoded by the first nucleotide sequence, wherein the one or more antimicrobial peptide(s) is selected from the group consisting of Microcin S (McsS, SEQ ID NO 9), CM 11 (SEQ ID NO 12), CM15 (SEQ ID NO 13) and Magainin 2 (SEQ ID NO 14);

(iii) a third nucleotide sequence encoding for a genetic inverter that inhibits expression of the second nucleotide sequence, wherein the genetic inverter is under control of an inducible promoter;

wherein the inducible promoter is induced, if the complex of the at least one protein encoded by the first nucleotide sequence and the marker molecule indicating the presence of said microorganism is below a threshold concentration and is not induced, if the complex of the at least one protein encoded by the first nucleotide sequence and the marker molecule indicating the presence of said microorganism exceeds a threshold concentration; and wherein the inducible promoter controlling the genetic inverter is the Qrr4 promoter (SEQ ID NO 4).

9. The recombinant cell of claim 8, wherein the recombinant cell is a genetically engineered prokaryotic cell.

10. The recombinant cell of claim 9, wherein the prokaryotic cell is a probiotic bacterium.

11. The recombinant cell of claim 10, wherein the prokaryotic cell is an *Escherichia coli* cell.

12. The recombinant cell of claim 11, wherein the *Escherichia coli* cell is a probiotic *E. coli* Nissle cell.

* * * * *